US008241329B2

(12) United States Patent
Abdou

(10) Patent No.: US 8,241,329 B2
(45) Date of Patent: Aug. 14, 2012

(54) DEVICE AND METHOD FOR THE PREVENTION OF MULTI-LEVEL VERTEBRAL EXTENSION

(76) Inventor: M. Samy Abdou, San Diego, CA (US)

(*) Notice: Subject to any disclaimer, the term of this patent is extended or adjusted under 35 U.S.C. 154(b) by 201 days.

(21) Appl. No.: 12/498,222

(22) Filed: Jul. 6, 2009

(65) Prior Publication Data

US 2010/0069965 A1 Mar. 18, 2010

Related U.S. Application Data

(60) Provisional application No. 61/133,858, filed on Jul. 5, 2008.

(51) Int. Cl.
*A61B 17/70* (2006.01)

(52) U.S. Cl. .......................... 606/247; 606/248; 606/279

(58) Field of Classification Search ........... 606/246–279
See application file for complete search history.

(56) References Cited

U.S. PATENT DOCUMENTS

| 5,609,634 | A | | 3/1997 | Voydeville | |
|---|---|---|---|---|---|
| 5,645,599 | A | | 7/1997 | Samani | |
| 6,132,464 | A | * | 10/2000 | Martin | 623/17.15 |
| 6,332,882 | B1 | | 12/2001 | Zucherman et al. | |
| 6,364,883 | B1 | * | 4/2002 | Santilli | 606/279 |
| 6,419,676 | B1 | | 7/2002 | Zucherman et al. | |
| 6,451,019 | B1 | | 9/2002 | Zucherman et al. | |
| 6,451,020 | B1 | | 9/2002 | Zucherman et al. | |
| 6,514,256 | B2 | | 2/2003 | Zucherman et al. | |
| 6,565,605 | B2 | * | 5/2003 | Goble et al. | 623/17.11 |
| 6,695,842 | B2 | | 2/2004 | Zucherman et al. | |
| 6,699,246 | B2 | | 3/2004 | Zucherman et al. | |
| 6,761,720 | B1 | | 7/2004 | Senegas | |
| 7,377,942 | B2 | * | 5/2008 | Berry | 623/17.11 |
| 7,588,589 | B2 | * | 9/2009 | Falahee | 606/247 |
| 7,695,514 | B2 | * | 4/2010 | Kwak | 623/17.11 |
| 7,708,765 | B2 | * | 5/2010 | Carl et al. | 606/279 |
| 2005/0033434 | A1 | * | 2/2005 | Berry | 623/17.14 |
| 2005/0267579 | A1 | * | 12/2005 | Reiley et al. | 623/17.11 |
| 2009/0024166 | A1 | * | 1/2009 | Carl et al. | 606/247 |
| 2009/0248078 | A1 | * | 10/2009 | Dant | 606/246 |
| 2011/0060366 | A1 | * | 3/2011 | Heim et al. | 606/247 |
| 2011/0106163 | A1 | * | 5/2011 | Hochschuler et al. | 606/264 |

* cited by examiner

*Primary Examiner* — Eduardo C Robert
*Assistant Examiner* — James Palmer
(74) *Attorney, Agent, or Firm* — Gazdzinski & Associates, PC

(57) ABSTRACT

Methods and devices are adapted to limit the extent of vertebral extension between an upper-most vertebral bone and a lower-most vertebral bone wherein a least one additional vertebral bone resides between them. In an embodiment, the limitation of extension occurs while flexion is at least partially maintained within at least one FSU. In other embodiments, flexion may be abolished.

40 Claims, 28 Drawing Sheets

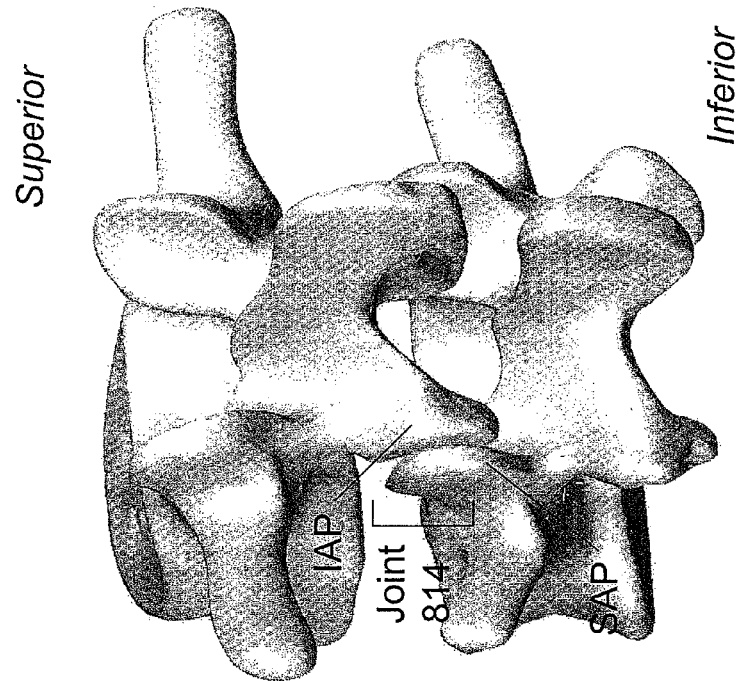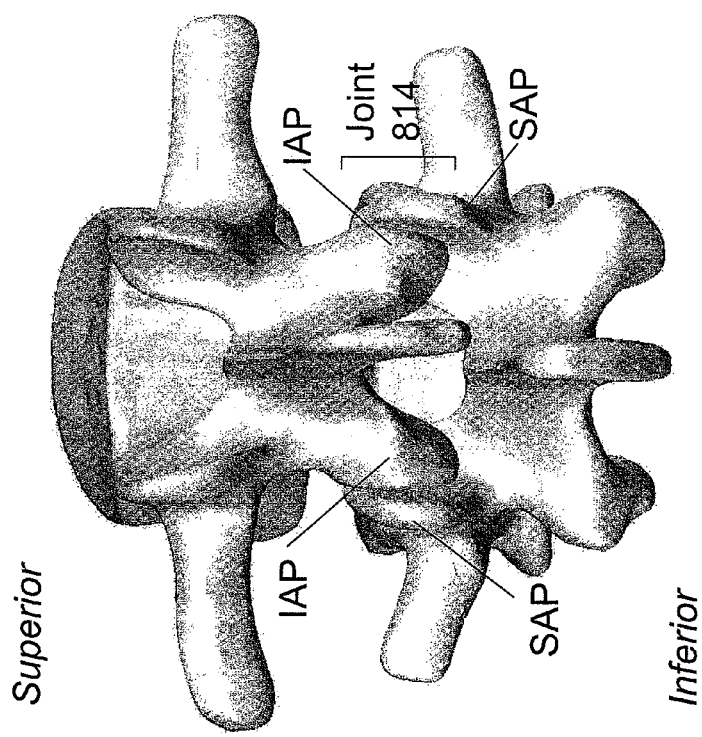

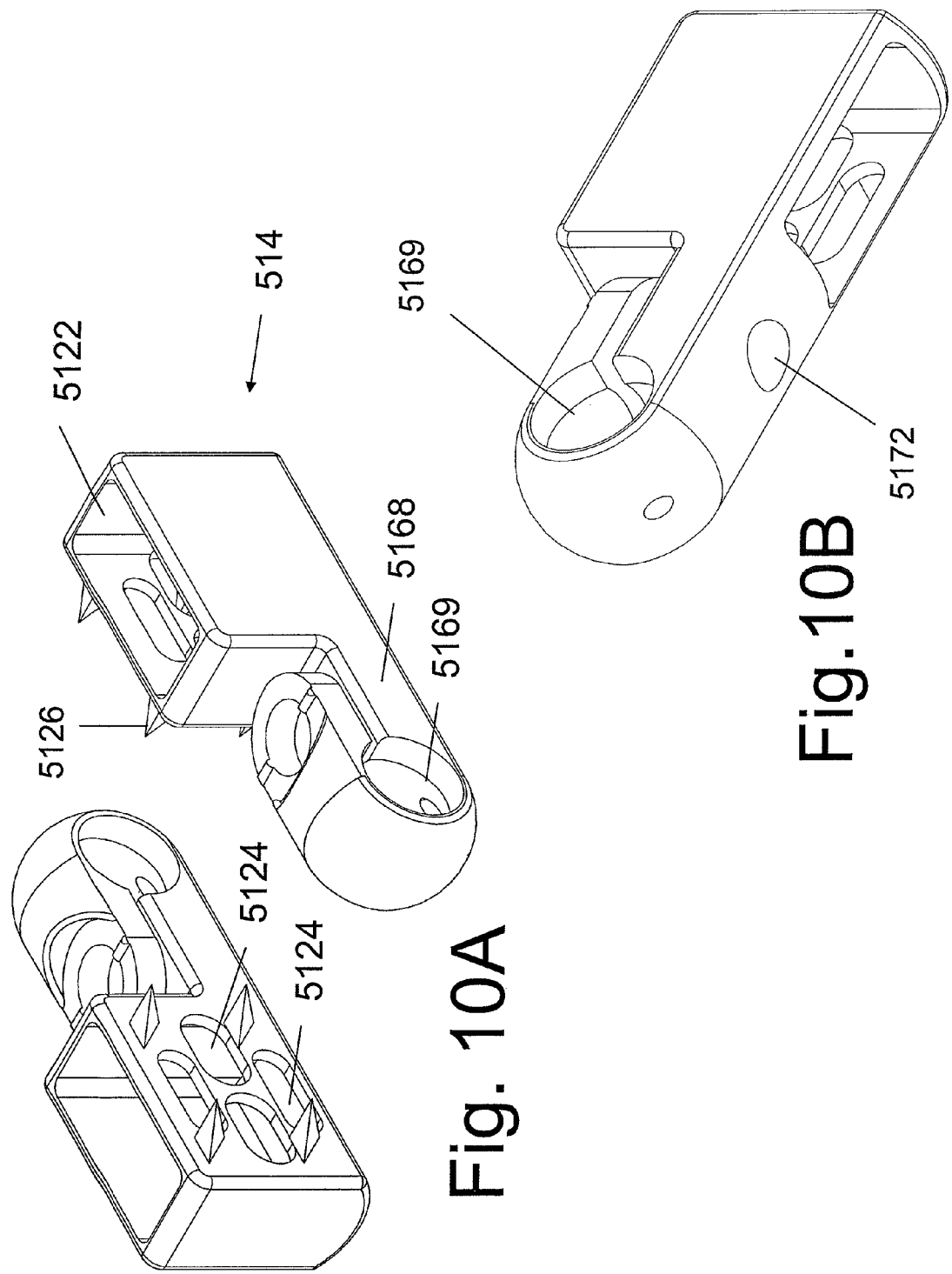

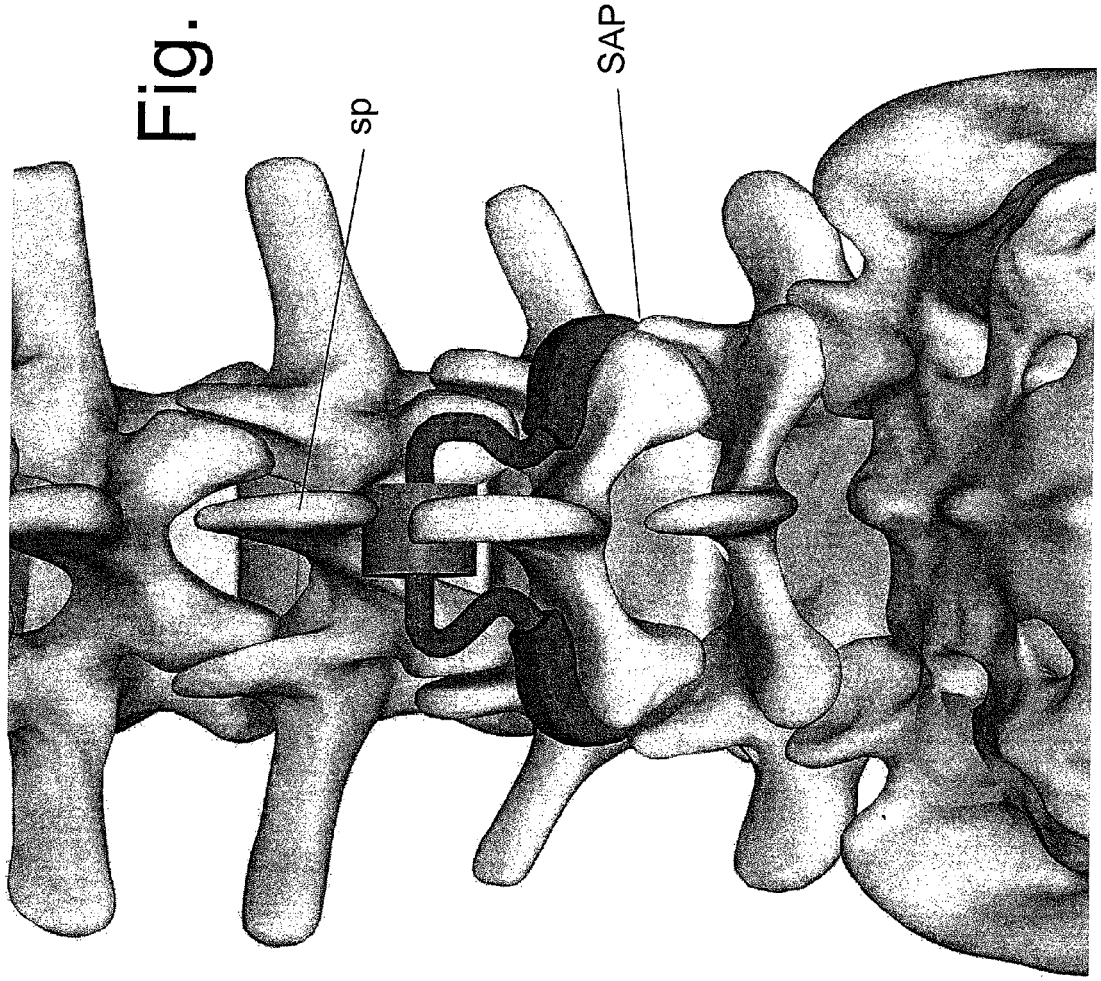

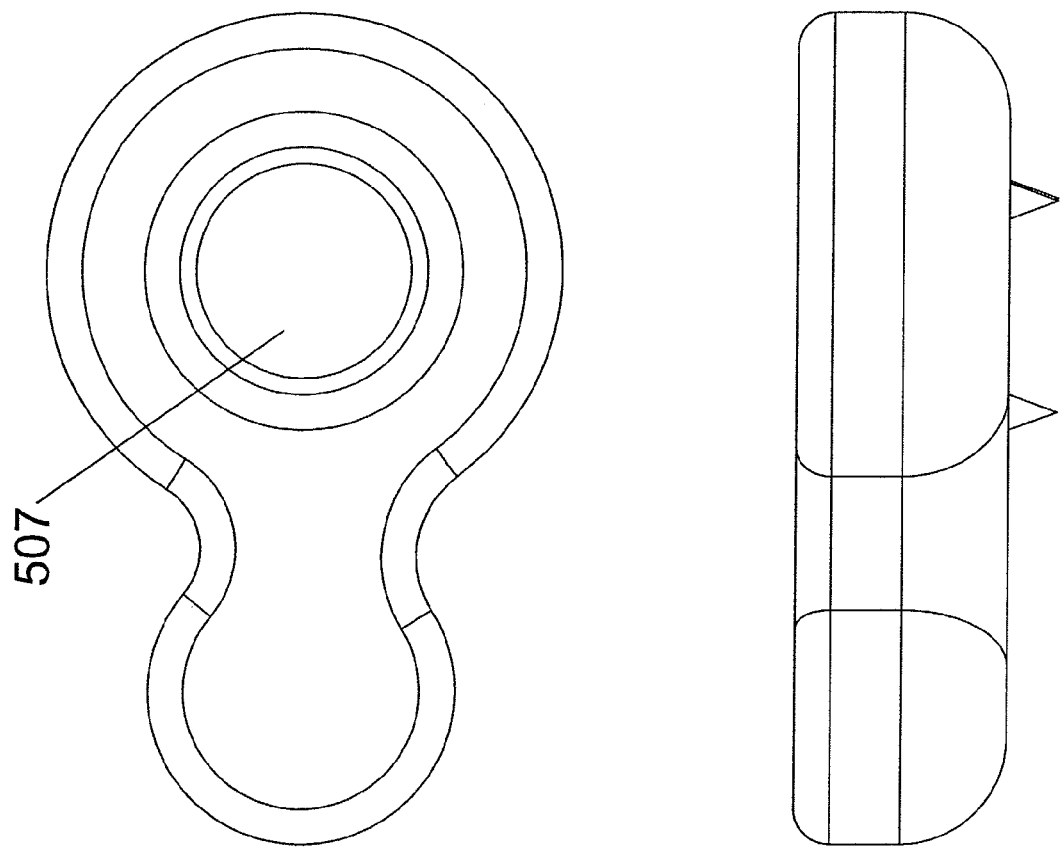
Fig. 21
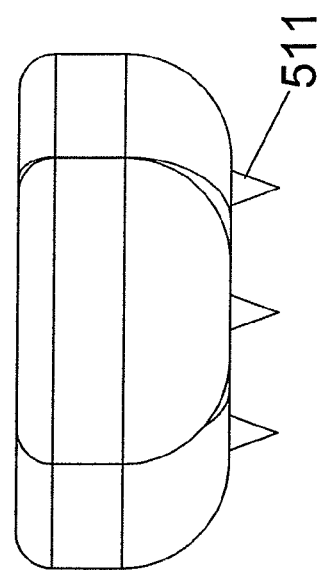

825

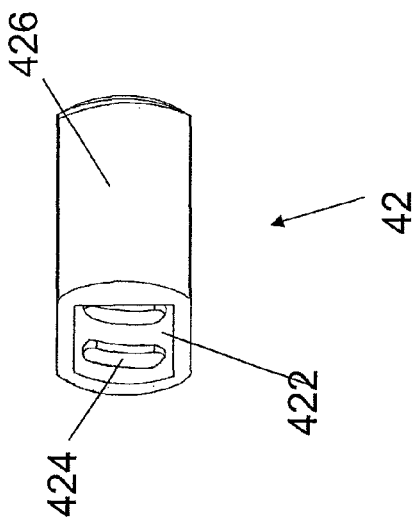
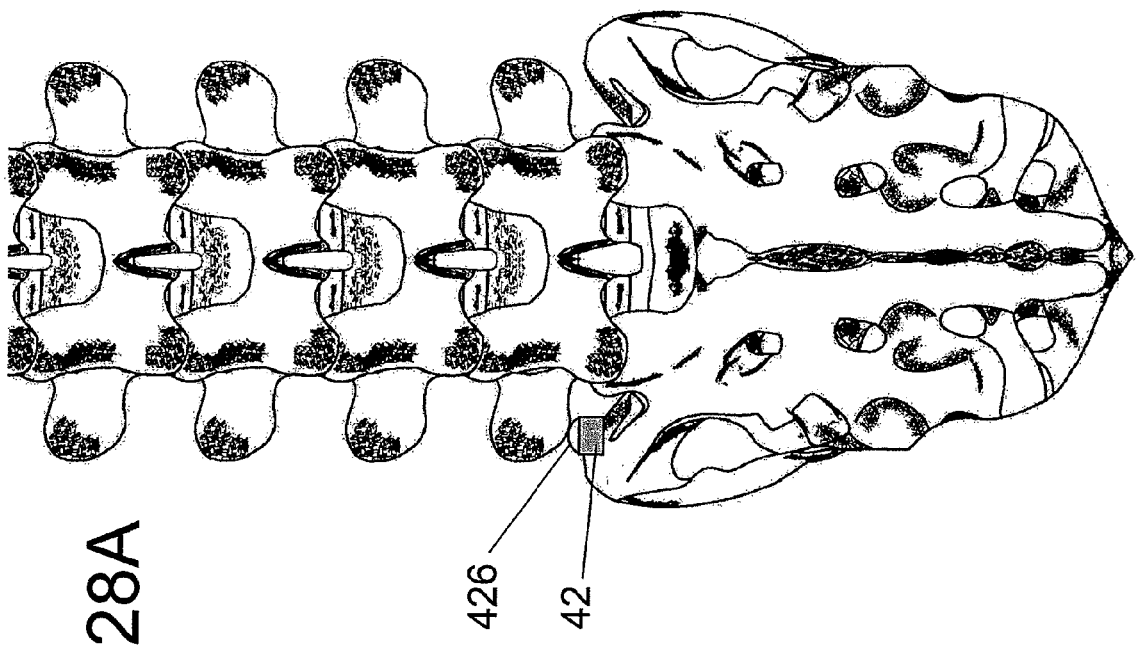

DEVICE AND METHOD FOR THE PREVENTION OF MULTI-LEVEL VERTEBRAL EXTENSION

REFERENCE TO PRIORITY DOCUMENT

This application claims priority of U.S. Provisional Patent Application Ser. No. 61/133,858, filed Jul. 5, 2008. Priority of the aforementioned filing date is hereby claimed and the disclosure of the Provisional Patent Application is hereby incorporated by reference in its entirety.

BACKGROUND

Progressive constriction of the central canal within the spinal column is a predictable consequence of aging. As the spinal canal narrows, the nerve elements that reside within it become progressively more crowded. Eventually, the canal dimensions become sufficiently small so as to significantly compress the nerve elements and produce pain, weakness, sensory changes, clumsiness and other manifestation of nervous system dysfunction.

Constriction of the canal within the lumbar spine is termed lumbar stenosis. This condition is very common in the elderly and causes a significant proportion of the low back pain, lower extremity pain, lower extremity weakness, limitation of mobility and the high disability rates that afflict this age group. The traditional treatment for this condition has been the surgical removal of the bone and ligamentous structures that constrict the spinal canal. Despite advances in surgical technique, spinal decompression surgery can be an extensive operation with risks of complication from the actual surgical procedure and the general anesthetic that is required to perform it. Since many of these elderly patients are in frail health, the risk of developing significant peri-operative medical problems remains high. In addition, the traditional treatment of surgical resection of spinal structures may relieve the neural compression but lead to spinal instability in a substantial minority of patients. That is, removal of the spinal elements that compress the nerves may cause the spinal elements themselves to move in an abnormal fashion relative to one another and produce pain. Should it develop, instability would require additional and even more extensive surgery in order to re-establish spinal stability. Because of these and other issues, elderly patients with lumbar stenosis must often choose between living the remaining years in significant pain or enduring the potential life-threatening complications of open spinal decompression surgery.

Recently, lumbar stenosis has been treated by the distraction—instead of resection—of those tissues that compress the spinal canal. In this approach, an implantable device is placed between the spinous processes of the vertebral bodies at the stenotic level in order to limit the extent of bone contact during spinal extension. Since encroachment upon the nerve elements occurs most commonly and severely in extension, this treatment strategy produces an effective increase in the size of the spinal canal by limiting the amount of spinal extension. In effect, the distraction of the spinous processes changes the local bony anatomy and decompress the nerves at the distracted level by placing the distracted spinal segment into slight flexion.

A number of devices that utilize this strategy have been disclosed. U.S. Pat. Nos. 6,451,020; 6,695,842; 5,609,634; 5,645,599; 6,451,019; 6,761,720; 6,332,882; 6,419,676; 6,514,256; 6,699,246 and other illustrate various spinous process distractors. Unfortunately, these patents disclosed device that distract one level at a time and often can not be applied at the L5/S1 level. Since disease at both L4/5 and L5/S1 is estimated to afflict more that 30% of this patient population, a need still remains for the development of devices that can simultaneously treat both levels.

SUMMARY

This application discloses a series of novel implants for spinal decompression and methods of minimally invasive device placement.

In one aspect, there is disclosed a method to limit the extent of vertebral extension between an upper-most vertebral bone and a lower-most vertebral bone of a spinal segment of three or more vertebrae, comprising: affixing an orthopedic device to an intermediate vertebral bone; abutting a member of the orthopedic device against an upper aspect of a portion of the superior articulating process of the lower-most vertebral bone of the spinal segment; abutting a member of the orthopedic device against a lower aspect of a portion of the inferior articulating process of the upper-most vertebral bone of the spinal segment; and limiting the travel of the superior articulating process of the lower-most vertebral bone towards the inferior articulating process of the upper-most vertebral bone during vertebral extension.

In another aspect, there is disclosed a method to limit the extent of vertebral extension between an upper-most vertebral bone and a lower-most vertebral bone within a spinal segment of three or more vertebrae, comprising: affixing an orthopedic device to the spinous process of the upper-most vertebral bone; abutting a member of the orthopedic device against an upper aspect of a portion of the superior articulating process of the lower-most vertebral bone; and limiting the travel of the superior articulating process of the lower-most vertebral bone towards the spinous process of the upper-most vertebral bone during vertebral extension.

Other features and advantages should be apparent from the following description of various embodiments, which illustrate, by way of example, the principles of the disclosed devices and methods.

BRIEF DESCRIPTION OF THE DRAWINGS

FIGS. 2A and 2B show views of two vertebral bones in a functional spinal unit.

FIGS. 10A and 10B shows a member of the first device embodiment.

FIGS. 11, 12A and 12B illustrate an additional device embodiment.

FIGS. 20, 21 and 22 show the device embodiment for the method of FIG. 19.

FIGS. 28A and 28B shows an alternate embodiment.

DETAILED DESCRIPTION

In order to promote an understanding of the principals of the invention, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one skilled in the art.

Figure 1:
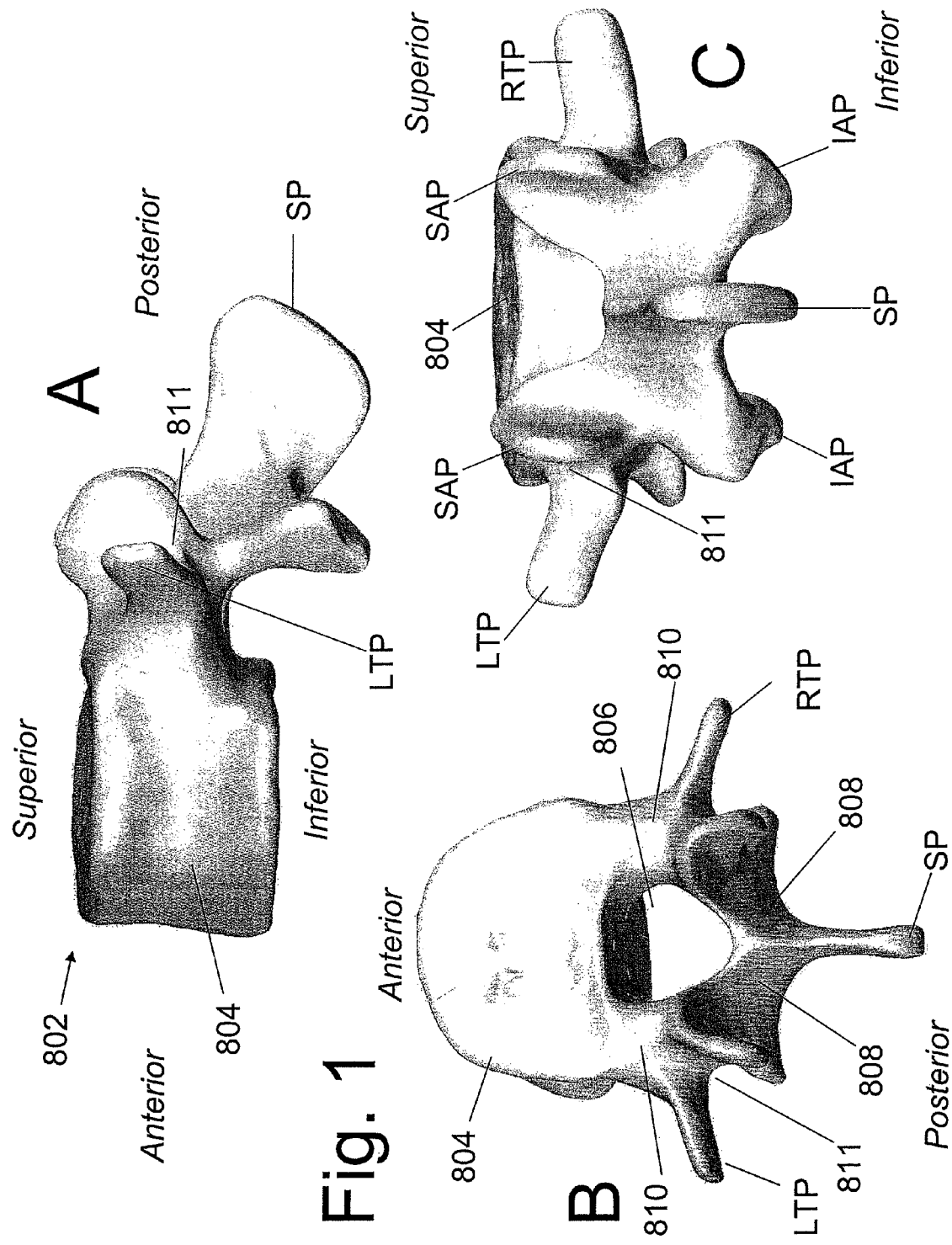
FIG. 1 illustrates multiple views of a vertebral bone.

FIG. 1 shows a diagrammatic representation of a spinal vertebral bone 802 in multiple views. For clarity of illustration, the vertebral bone of FIG. 1 and those of other illustrations presented in this application are represented schematically and those skilled in the art will appreciate that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. Thus, the disclosed devices and methods may be applied at any applicable spinal level.

Vertebral bone 802 contains an anteriorly-placed vertebral body 804, a centrally placed spinal canal and 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIG. 2 where intervertebral disc would reside.) FIG. 2A shows the posterior surface of the adjacent vertebrae and the articulations between them while FIG. 2B shows an oblique view. Note that FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone.

The preceding illustrations and definitions of anatomical structures are known to those of ordinary skill in the art. They are described in more detail in *Atlas of Human Anatomy*, by Frank Netter, third edition, *Icon Learning Systems*, Teterboro, N.J. The text is hereby incorporated by reference in its entirety.

Figure 3B:
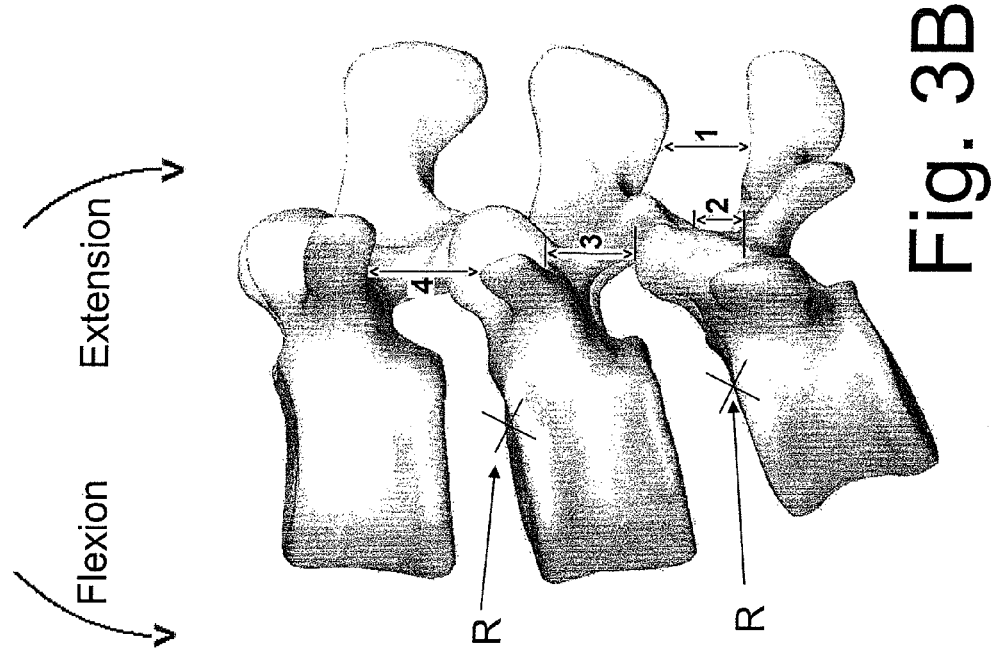
FIGS. 3A and 3B show views of three vertebral bones.
Figure 3A:
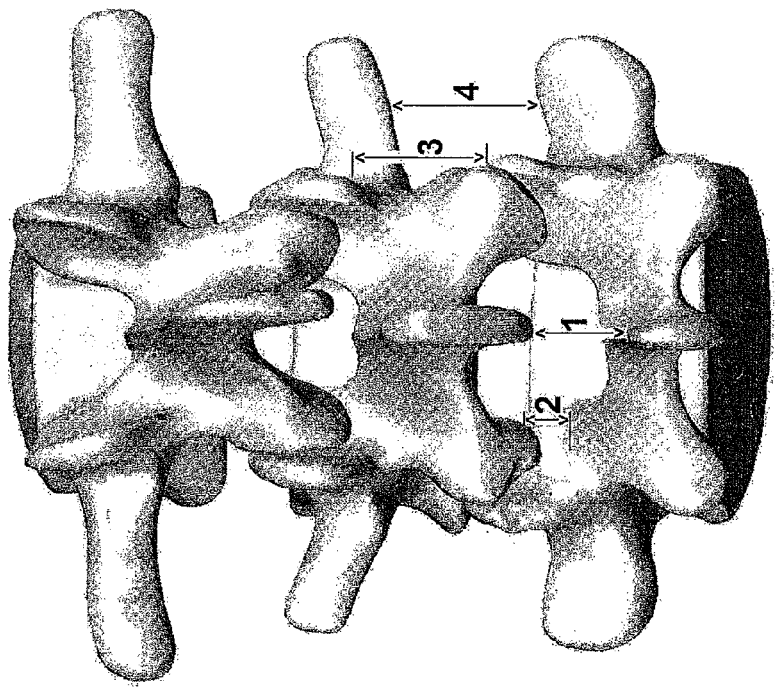

FIGS. 3A and 3B illustrate a view of the posterior aspect and the lateral aspect of three vertebral bones, which make up two functional spinal units (FSU). As shown in FIG. 3B, flexion of an upper vertebral bone relative to a lower vertebral bone within a FSU occurs about a center of rotation R, wherein the center of rotation R is physiologically positioned at or near the point illustrated in FIG. 3B. Similarly, extension of an upper vertebral bone relative to a lower vertebral bone within a FSU occurs at or near center of rotation R.

Disclosed are methods and devices that limit the extent of vertebral extension between an upper-most vertebral bone (hereto refers to the most superior vertebral bone of the spinal segment under treatment) and a lower-most vertebral bone (hereto refers to the most inferior vertebral bone of the spinal segment under treatment) wherein a least one additional vertebral bone resides between them. That is, the disclosed devices and methods are adapted to limit extension across at least three vertebral bones (or two functional spinal units). In an embodiment, the limitation of extension occurs while flexion is at least partially maintained within at least one FSU. In other embodiments, flexion may be abolished.

In FIGS. 3A and B, four distances are illustrated and labeled 1 through 4. While distance 1 is shown as the distance between the lower surface of the upper spinous process and the upper surface of the lower spinous process, it may be, alternatively, the distance between any points on each spinous process. Distance 2 is the distance between a segment of the inferior articulating process (IAP) (also sometimes called the "inferior facet") of an upper vertebra (or a point on the IAP, such as, for example, the inferior surface of the IAP) and a pre-determined point on the lamina of the lower vertebra (such as, for example, the center of the underlying pedicle). Distance 3 is the distance between a portion of the pedicel (and/or transverse process) of the upper vertebra and a portion of the superior articulating process (SAP) (also sometimes called the "superior facet") of the lower vertebra (such as, for example, the top of the SAP). Distance 4 is the distance between a segment of the transverse processes (or superior aspect of the sacral wing—also called the sacral ala—in the case of the S1 vertebra) of adjacent vertebral bones.

Since each of the defined four distances is located posterior to the center of rotation R, these distances must decrease in value with progressive extension between adjacent vertebral bones. Hence, implantation of a device that limits the decrease in any of the four distances during vertebral extension will necessarily limit the extent of vertebral extension. Further, a device or spacer that limits any one of these four distances between a first set of vertebrae and any one of these four distances between a second set of vertebrae may be used to limit extension between a top-most and a bottom-most vertebra within a group of three adjacent vertebrae. The concept can be further extended to limit extension between a top-most and a bottom-most vertebra within a spinal segment of more than three adjacent vertebrae by limiting any one of these four distances across each of the functional spinal units that define the spinal segment. (In general, a spinal column segment that contains an N number of vertebral bones will also contain an N-1 number of functional spinal units.)

Figure 4:
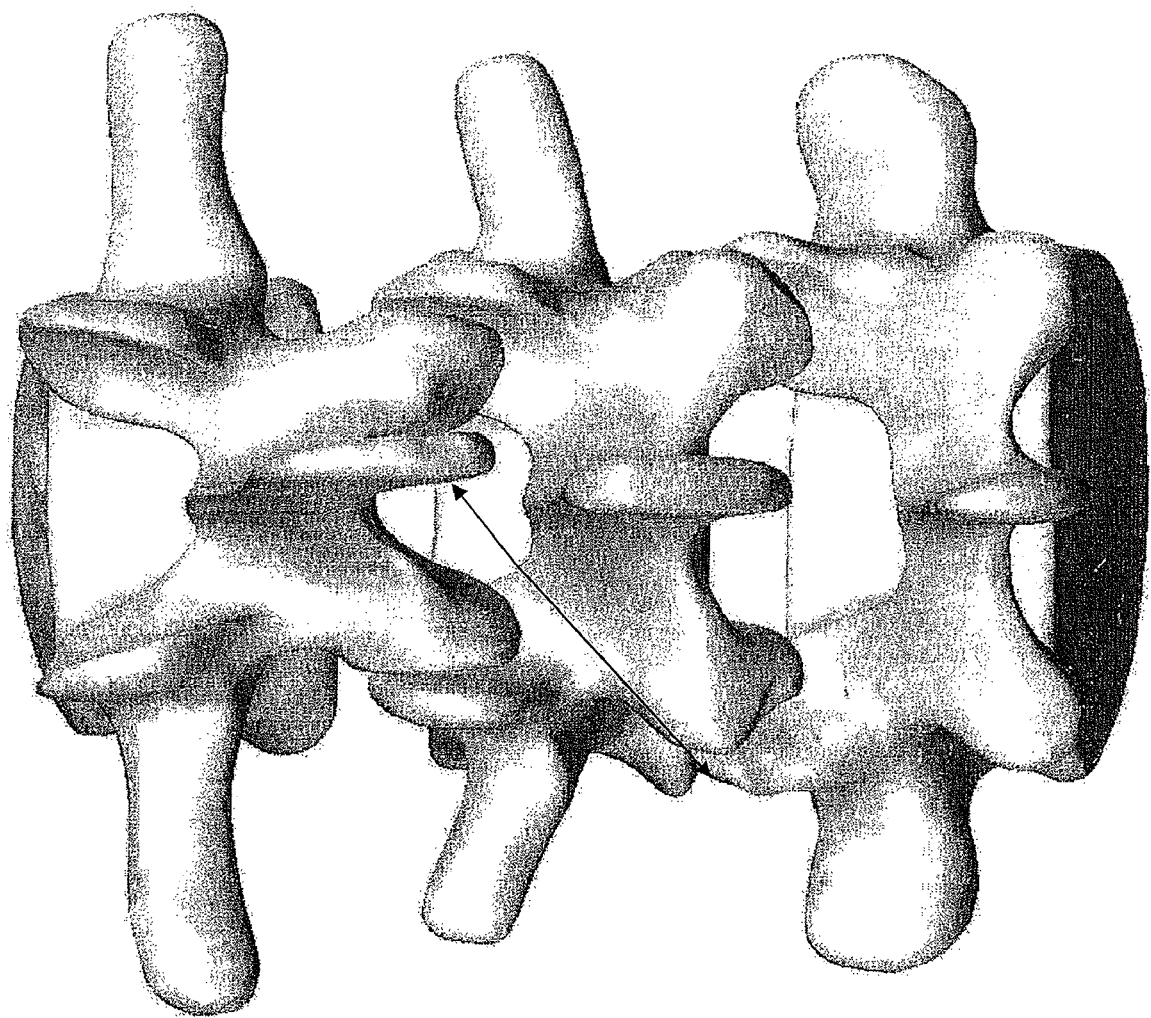
FIG. 4 illustrates a first method.
Figure 5:
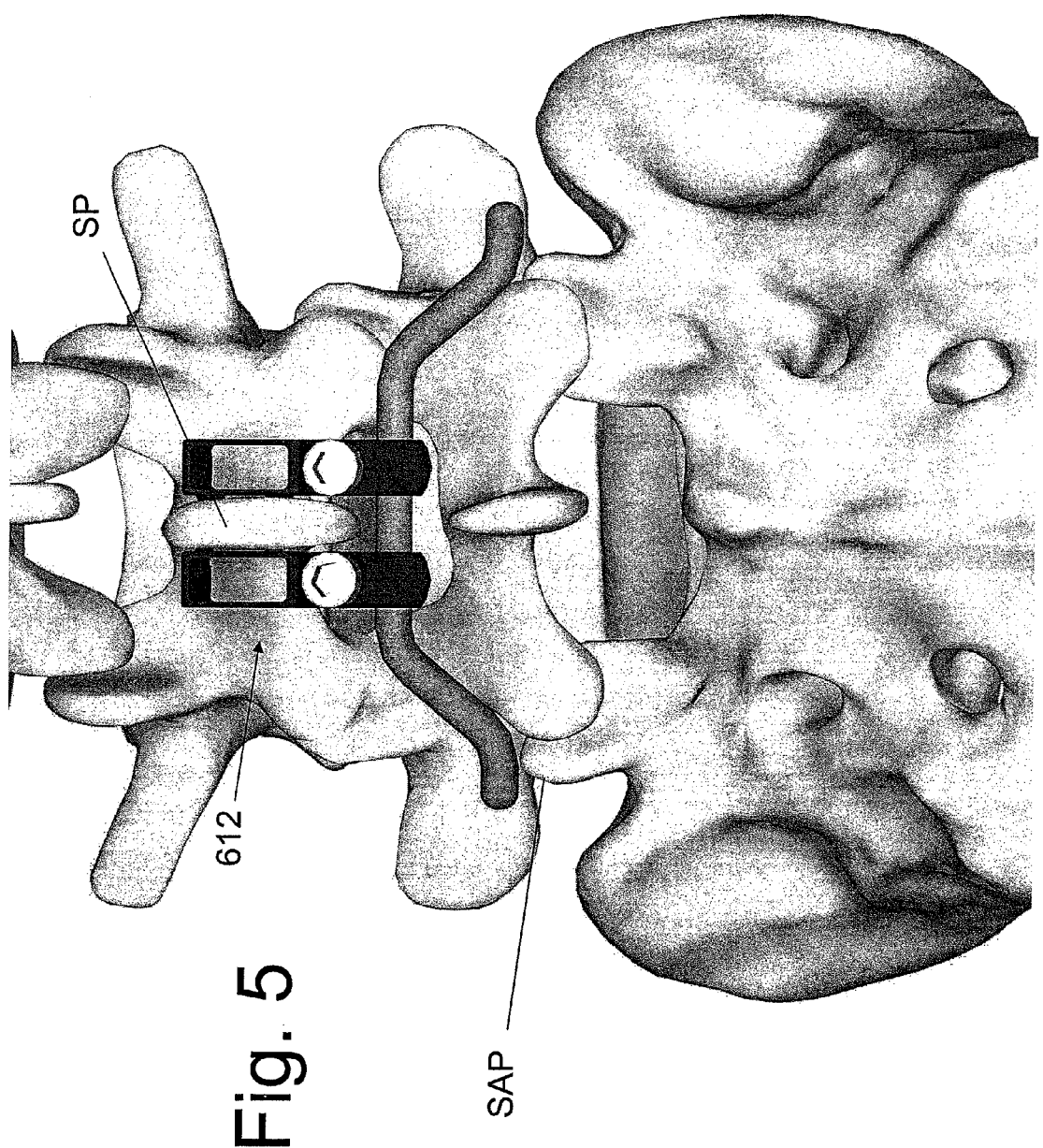
FIGS. 5, 6 and 7 show a first device embodiment.

Extension between a top-most and a bottom-most vertebra within a spinal segment of three or more vertebrae can also be limited by limiting the distance D1 (FIG. 4) between the spinous process of upper-most vertebra and SAP of the lower-most vertebra. An illustrative device embodiment is shown attached to the spine in FIGS. 5, 6 and 7. Device 612 is shown in an assembled configuration on FIG. 8 and in an exploded view in FIG. 9. The device contains a cavity adapted to accept bone graft or bone graft substitute (collectively referred to as bone graft material) that will form a direct bony fusion with a surface of the superior vertebra. The device further contains a surface adapted to abut the SAP of the lower-most vertebra, wherein, preferably but not necessarily, device 612 is not rigidly attach to the inferior-most vertebra. In this way, flexion between the upper and lower-most vertebras is not immobilized.

Figure 8:
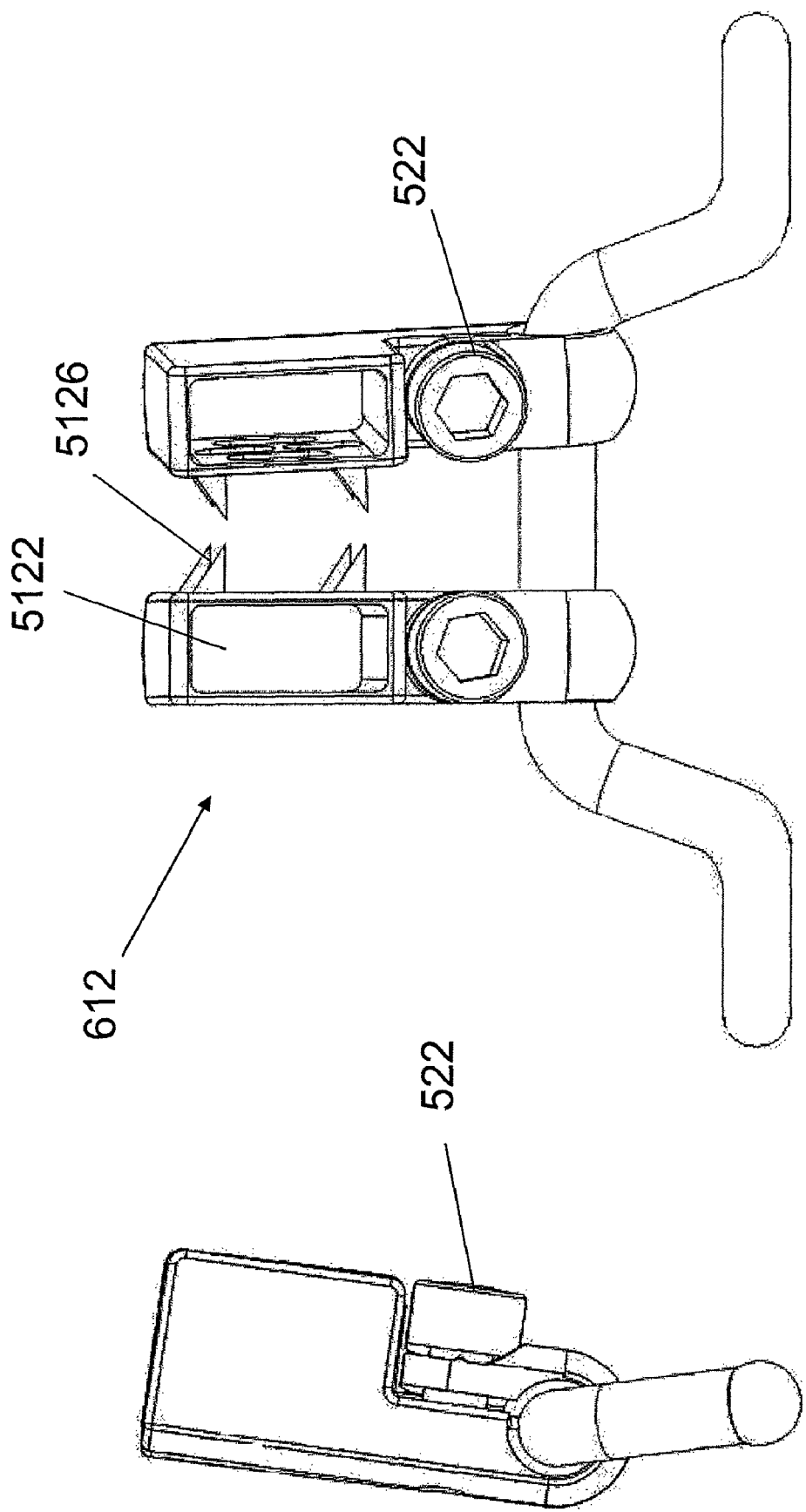
FIG. 8 shows an assembled view of the first device embodiment.

FIGS. 10A and 10B illustrate multiple perspective views of the central member 514 of device 612 shown in FIG. 8. The member 514 is substantially L-shaped and includes a main section with an internal compartment 5122 that is adapted to receive and house a bone graft or bone graft substitute. The main section includes multiple bores 5124 of variable size through the medial wall and/or bottom wall that borders the compartment 5122. The bores 5124 permit communication between the bone graft material within compartment 5122 and the adjacent spinal bone, so that a bony fusion could be established between the bone graft within compartment 5122 and the adjacent spinal segment. The member 514 also includes multiple spiked protrusions 5126 that permit device fixation to the adjacent bone. The member 514 further includes a segment 5168 that is split along a portion of itself. The segment 5168 defines a central bore 5169 that can be adjusted in size by virtue of one portion of the split segment 5168 moving relative to another portion along the split. A locking screw 522 can reside within a threaded bore 5172 of member 514.

Figure 9:
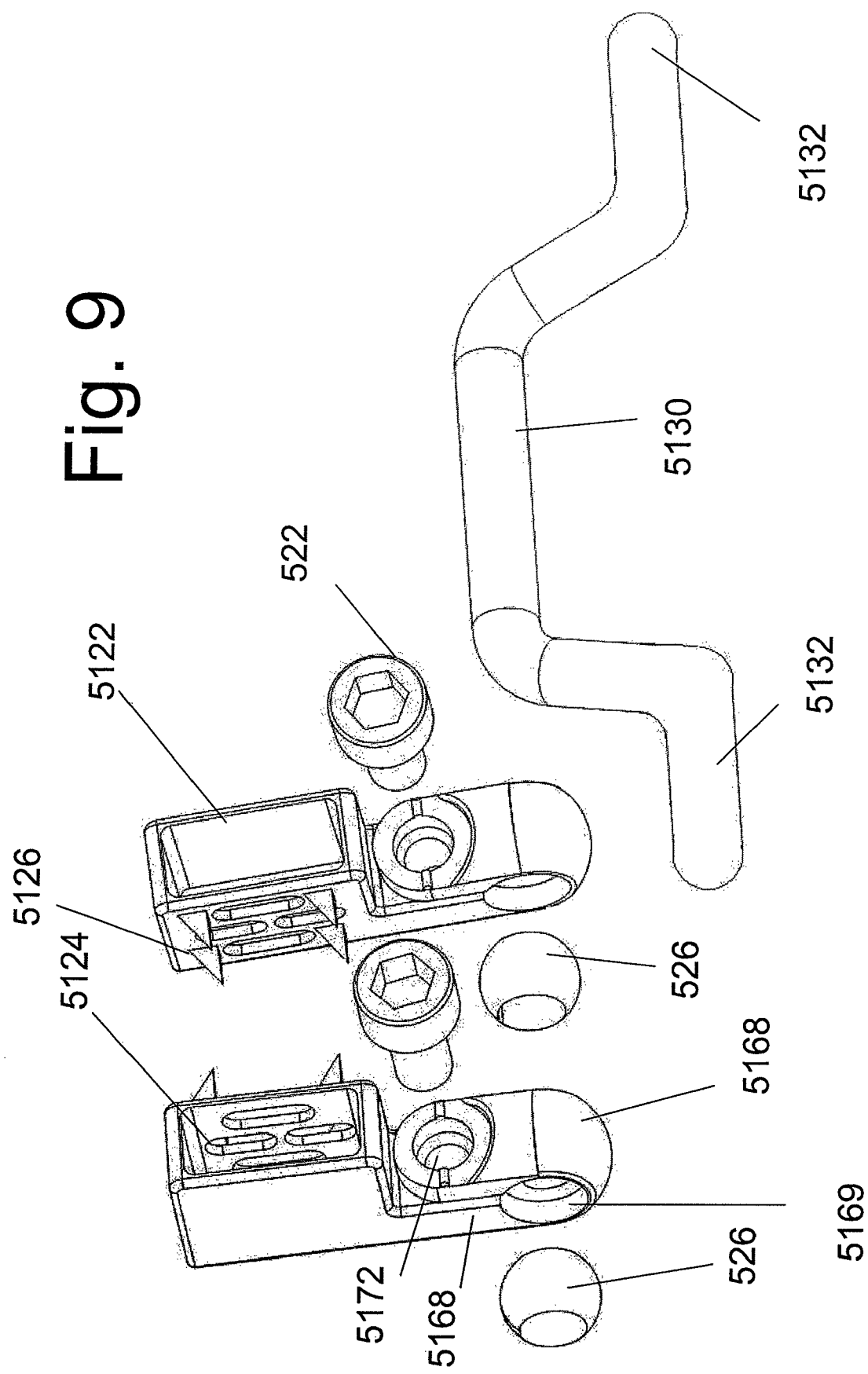
FIG. 9 shows an exploded view of the first device embodiment.

When device 612 is in the assembled state, a split locking sphere 526 resides within central bore 5169 of segment 5168, as shown in FIGS. 9 and 10. A bar 5130 resides within the central bore of the split locking sphere 526. Rotation and advancement of a threaded locking screw 522 within threaded bore 5172 produces closure of split segment 5168 and reduction of the diameter of central bore 5169. The split locking sphere 526 is compressed and the bar 5130 is immobilized relative to the member 512. In this way the device is rigidly locked.

In use, the bone surface of the lateral aspect of the spinous process and/or posterior surface of the lamina are denuded of soft tissue and decorticated in preparation for bone fusion. The device is applied to the spine, wherein the bar 5130 is moved into position so that each abutment bar 5132 is brought into contact with a segment (for example, the upper edge) of the superior articulating process (SAP) of the lower-most vertebra. This necessarily places abutment bar 5132 between the superior and inferior articulating processes of the vertebral bone (the intermediate vertebra) that is between the upper-most and lower-most vertebrae.

Figure 6:
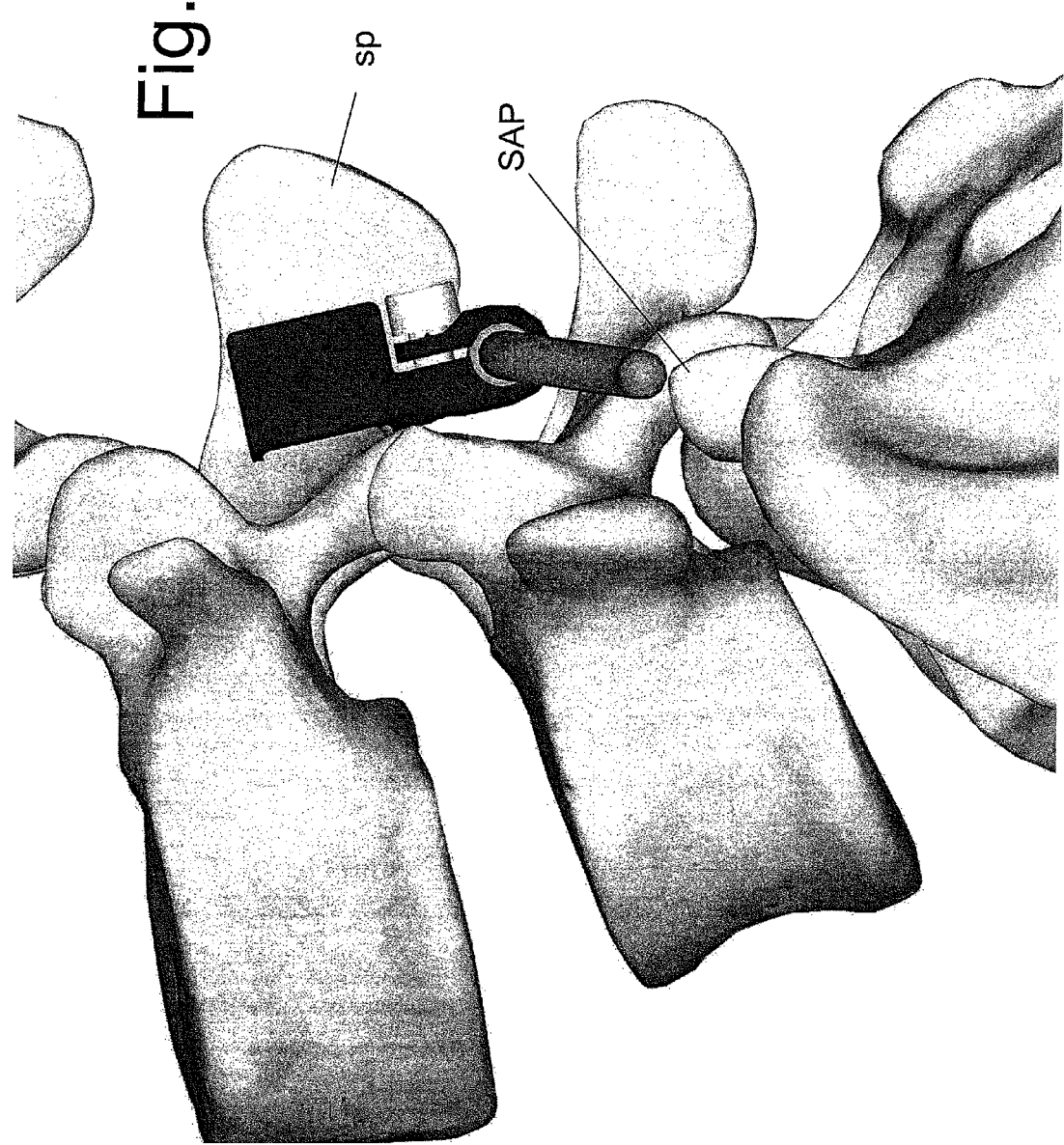
Figure 7:
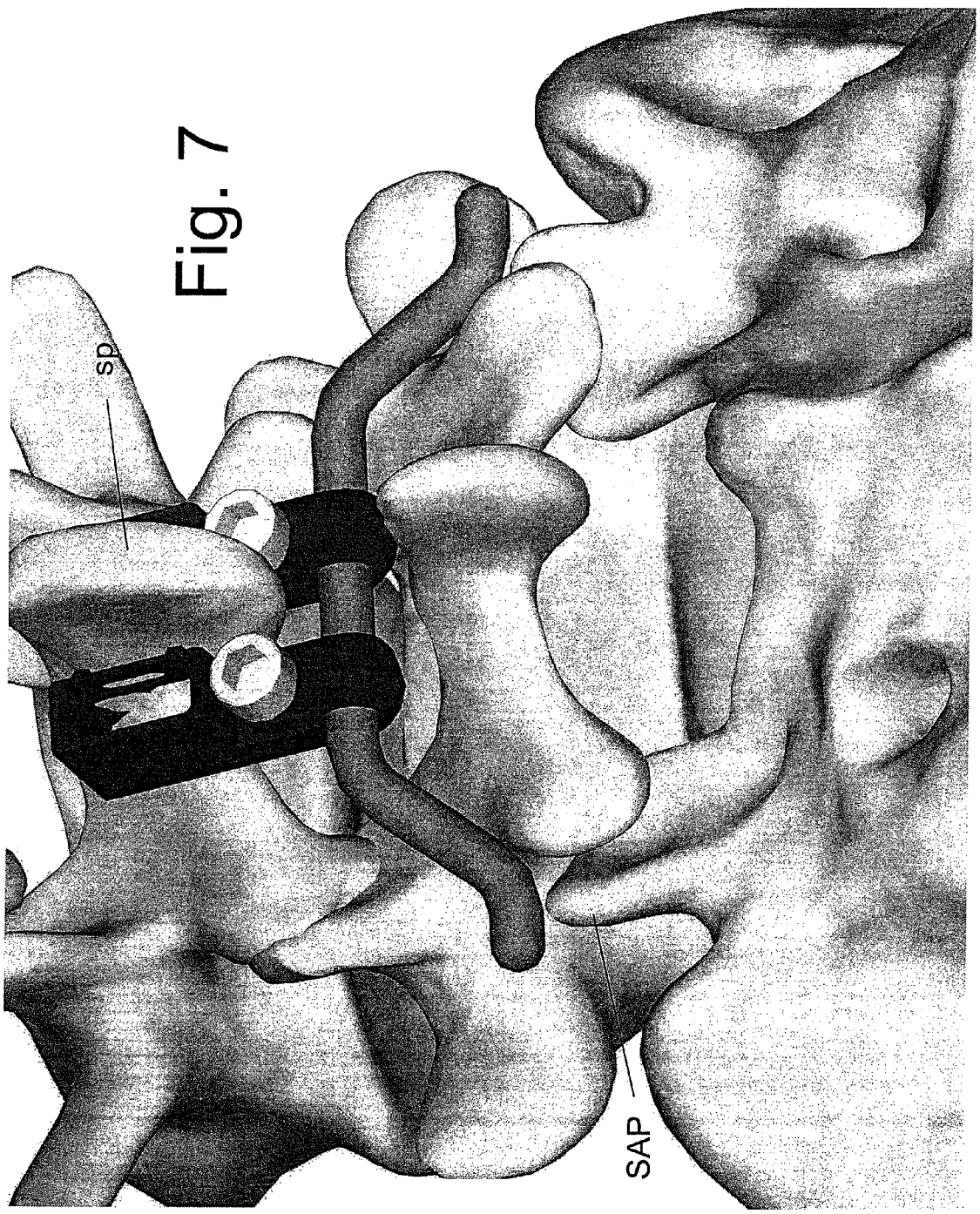

In application, each member 512 is then forced medially by a locking tool, such as, for example, a pair of pliers (not shown) so as drive spiked protrusions 5126 into the lateral aspect of the spinous process of the upper-most vertebra. Once positioned, abutment bars 5132 are moved into position so that they abut the SAP of the lower-most vertebra. A portion of bar 5130 may also be positioned to abut the posterior aspect of the lamina of the intermediate vertebra (as shown in FIGS. 6 and 7). In this way, device 512 also prevents the anterior translation of the upper-most vertebra relative to the intermediate vertebra. That is, in addition to limiting extension between the upper-most and lower-most vertebra, the device also prevents the formation or progression of an anterior spondylolisthesis between the upper-most and the intermediate vertebra.

After the bar is well positioned, each locking screw 522 is actuated so as to immobilize each member 512 relative to bar 5130. Bone graft material is packed into each compartment 5122, so that the bone graft material forcibly contacts the lateral wall of the spinous process and/or the posterior wall of the lamina of the upper-most vertebra.

Figures 12A, 12B:
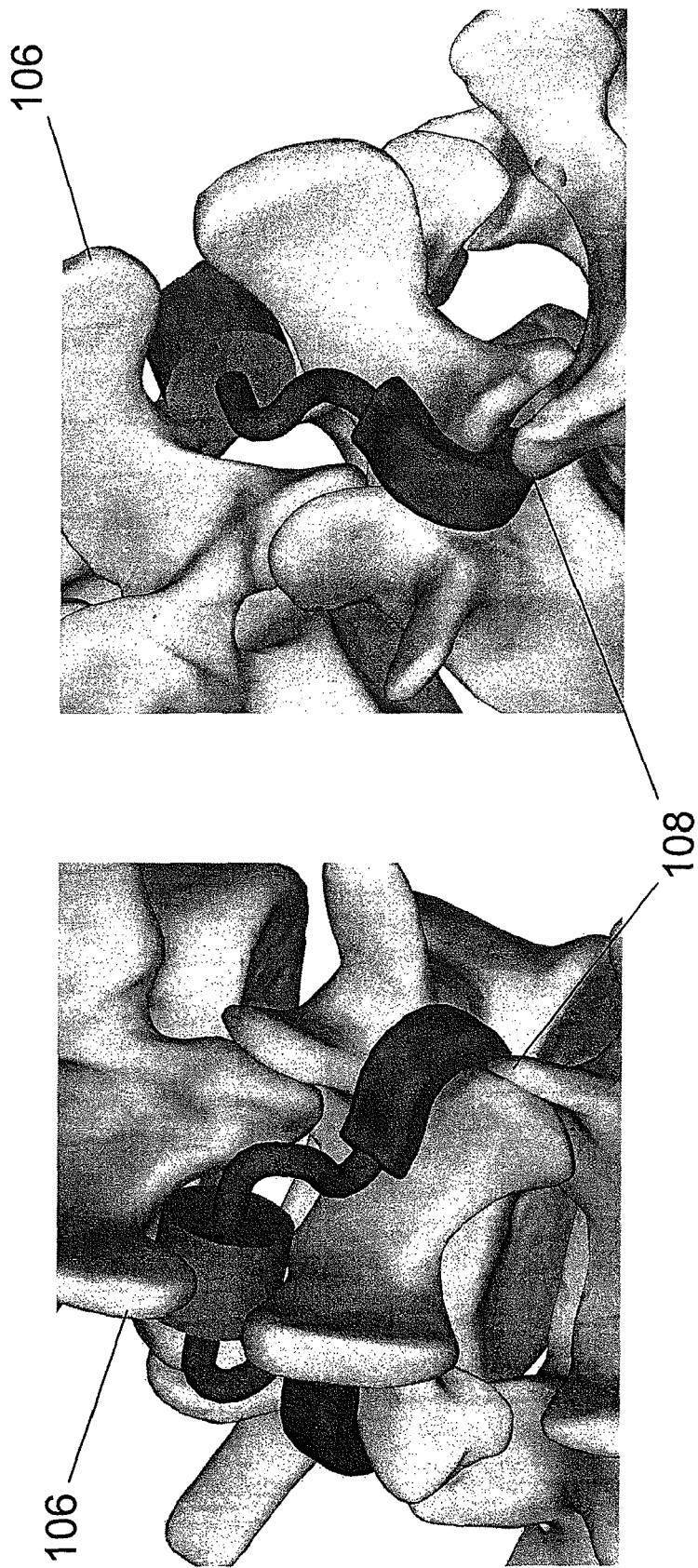

In an additional embodiment, the distance between the spinous process of the upper-most vertebra and the SAP of the lower-most vertebra is limited by the device such that there is relative prevention of vertebral extension (FIG. 11). The device contains a malleable segment 301 and an abutment segment 304, wherein segment 304 is adapted to be positioned between the spinous processes of the upper-most and intermediate vertebrae and maintain the distance between them. An additional abutment surface 306 is positioned between the SAP and IAP of the intermediate vertebra so as to overly the pars interarticularis portion of that vertebral bone. The inferior aspect of the abutment surface 306 is positioned to abut the superior aspect of the SAP of the lower-most vertebra, as shown in FIGS. 12A and B. The malleable segment 301 produces a compressive force between the two abutment surfaces 306 and keeps the implanted device attached to the intermediate vertebral bone.

Figure 13:
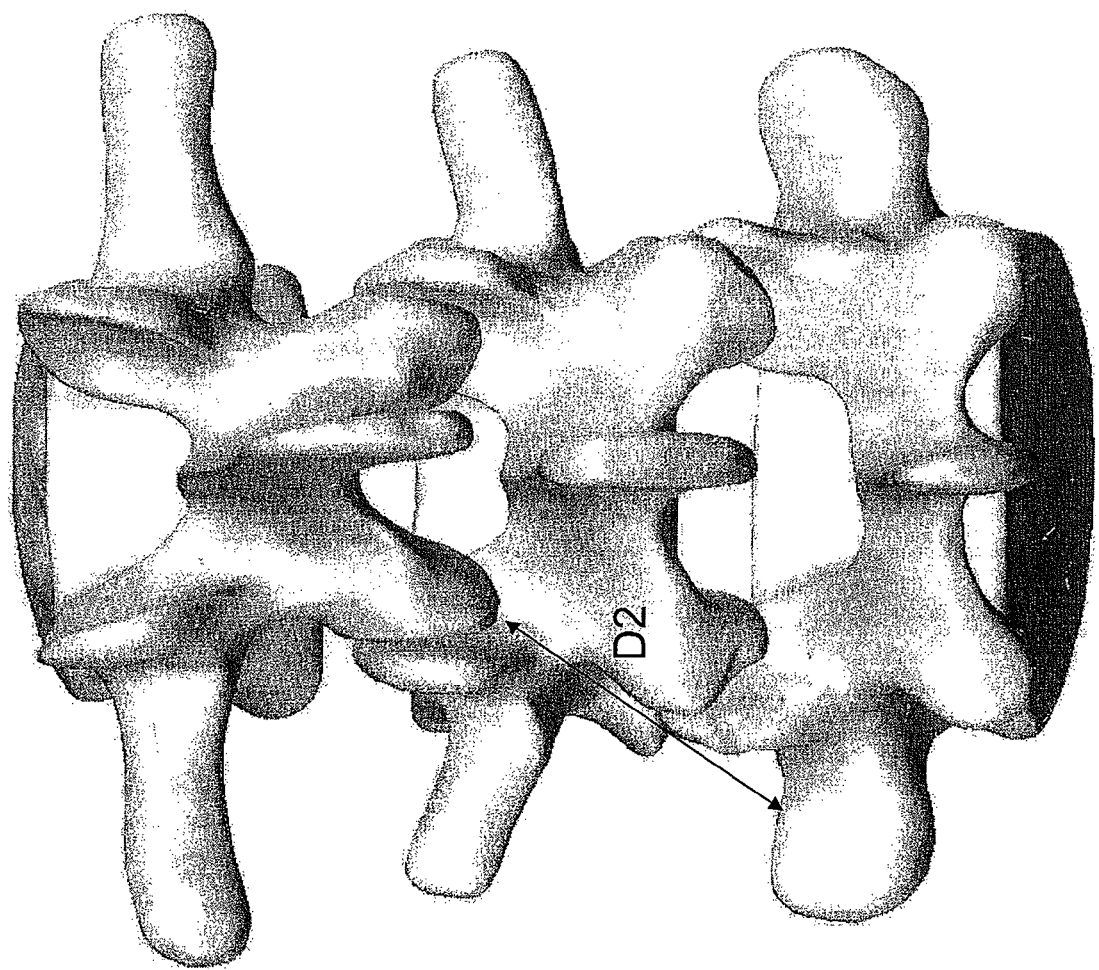
FIG. 13 illustrates an additional method.
Figure 14:
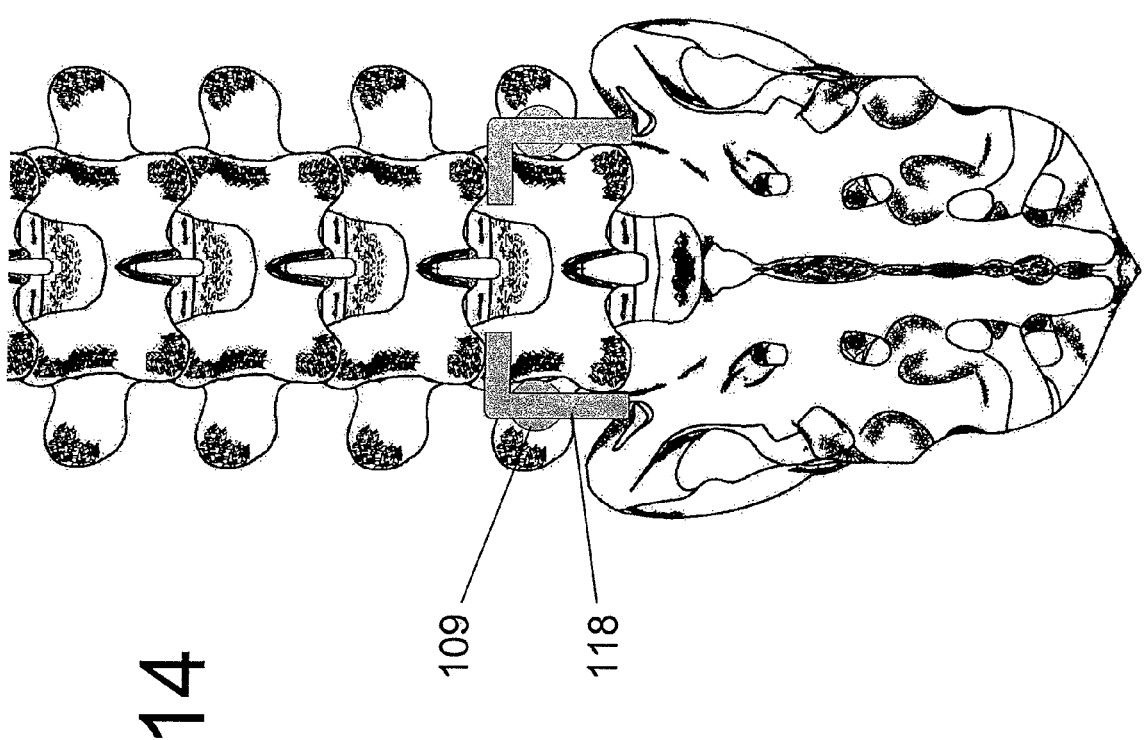
FIG. 14 shows the device embodiment for the method of FIG. 13.

In an additional embodiment, extension between a top-most and a bottom-most vertebra within a spinal segment of three or more vertebrae can also be limited by limiting the distance D2 (FIG. 13) between the inferior articulating process of the upper-most vertebra and transverse process (or the sacral ala at the sacral level) of the lower-most vertebra. FIG. 14 illustrates a device to accomplish the method of FIG. 13. A bone screw 109 or similar fastener is attached to the pedicle portion (or similar bone attachment point) of the intermediate vertebra. A bar 118 is attached to the bone screw on each side of the vertebral midline wherein the superior aspect of bar 118 abuts the inferior aspect of the IAP of the upper-most vertebra. The inferior surface of bar 118 abuts the superior aspect of the transverse process (top of sacral ala at S1) of the lower-most vertebra.

Figure 15B:
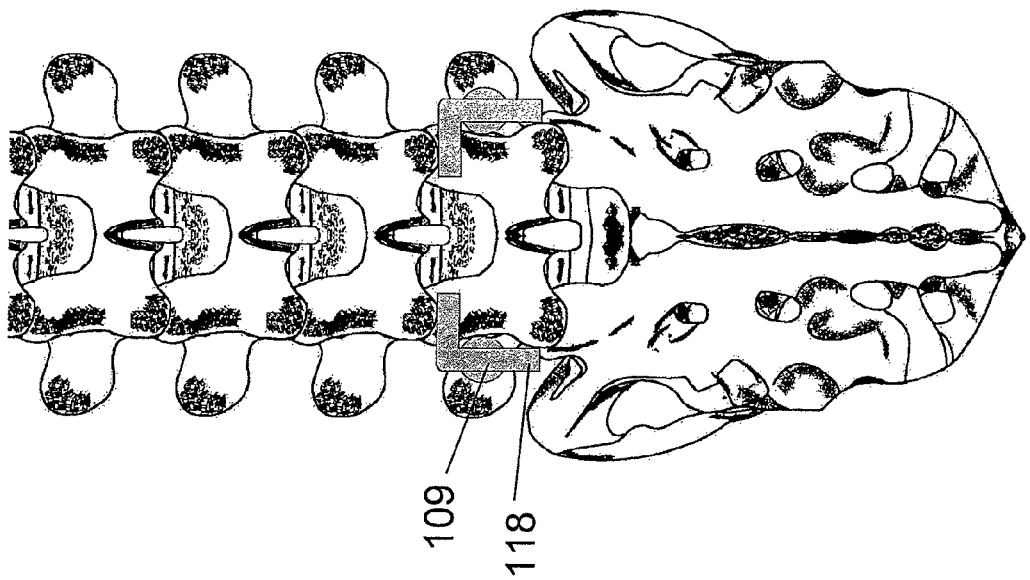
FIGS. 15A and 15B show an alternate embodiment.
Figure 15A:
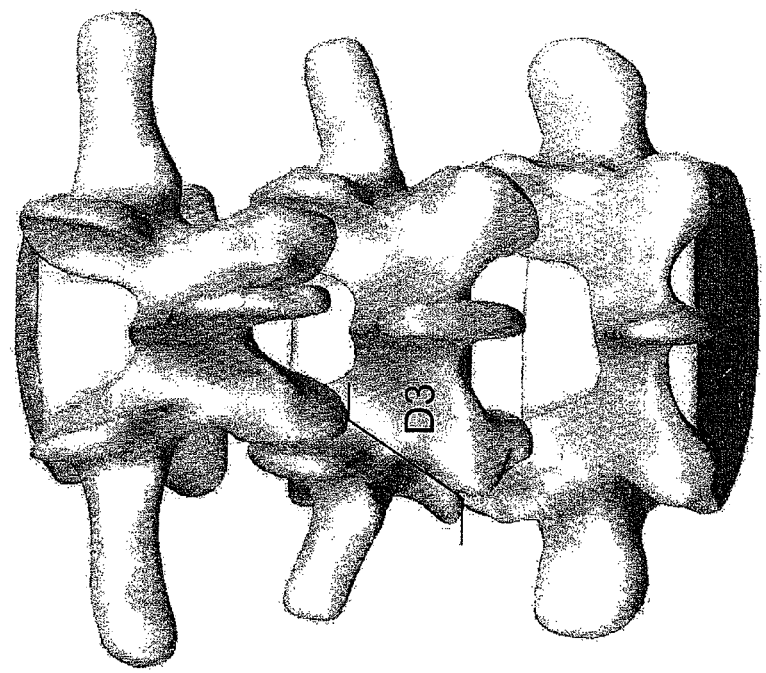

Alternatively, the inferior surface of bar 118 may be positioned to abut the superior aspect of the SAP of the lower-most vertebra, as shown in FIG. 15B. In this embodiment, extension between a top-most and a bottom-most vertebra within a spinal segment of three or more vertebrae is limited by limiting the distance D3 (shown in FIG. 15A).

Figure 16B:
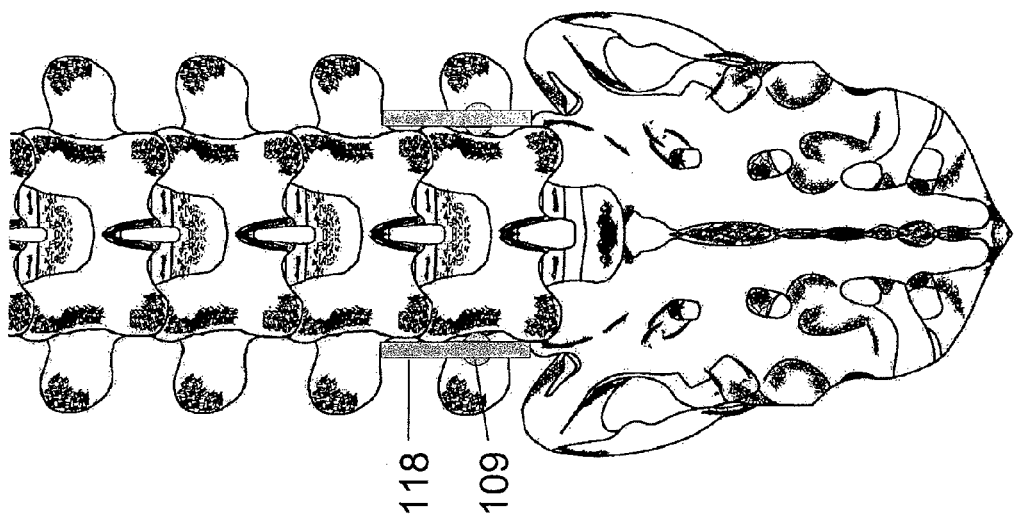
FIGS. 16A and 16B show an alternate embodiment.
Figure 16A:
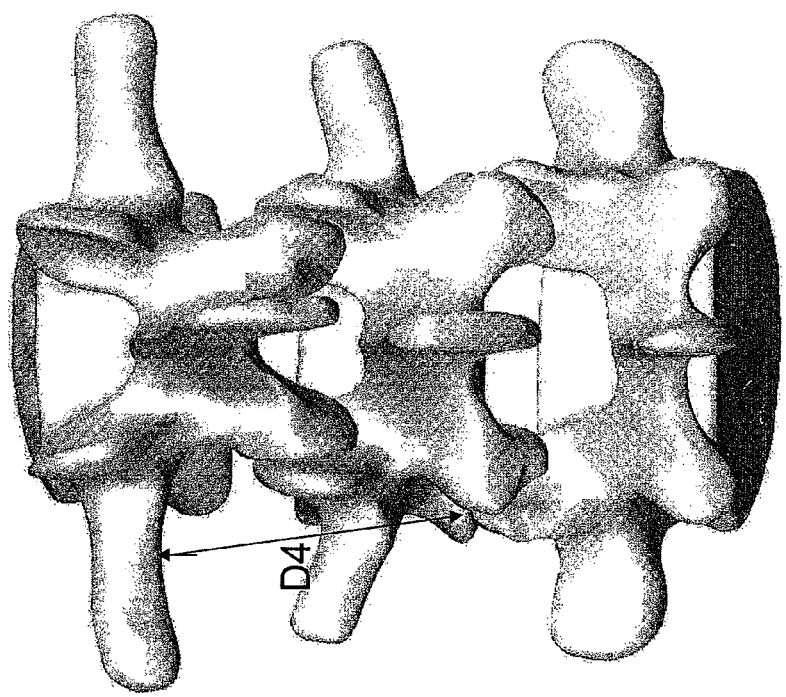

In another embodiment, extension between a top-most and a bottom-most vertebra within a spinal segment of three or more vertebrae is limited by limiting the distance D4 (FIG. 16A) between the transverse process of the upper-most vertebra and the SAP of the lower-most vertebra. FIG. 16B illustrates a device to accomplish the method of FIG. 16A. A bone screw 109 or similar fastener is attached to the pedicle portion (or similar bone attachment point) of the intermediate vertebra. A bar 118 is attached to the bone screw (preferably, but not necessarily, on each side of the vertebral midline) wherein the superior aspect of bar 118 abuts an inferior surface of the transverse process of the upper-most vertebra. The inferior surface of bar 118 abuts the superior aspect of the SAP of the lower-most vertebra.

Figure 17:
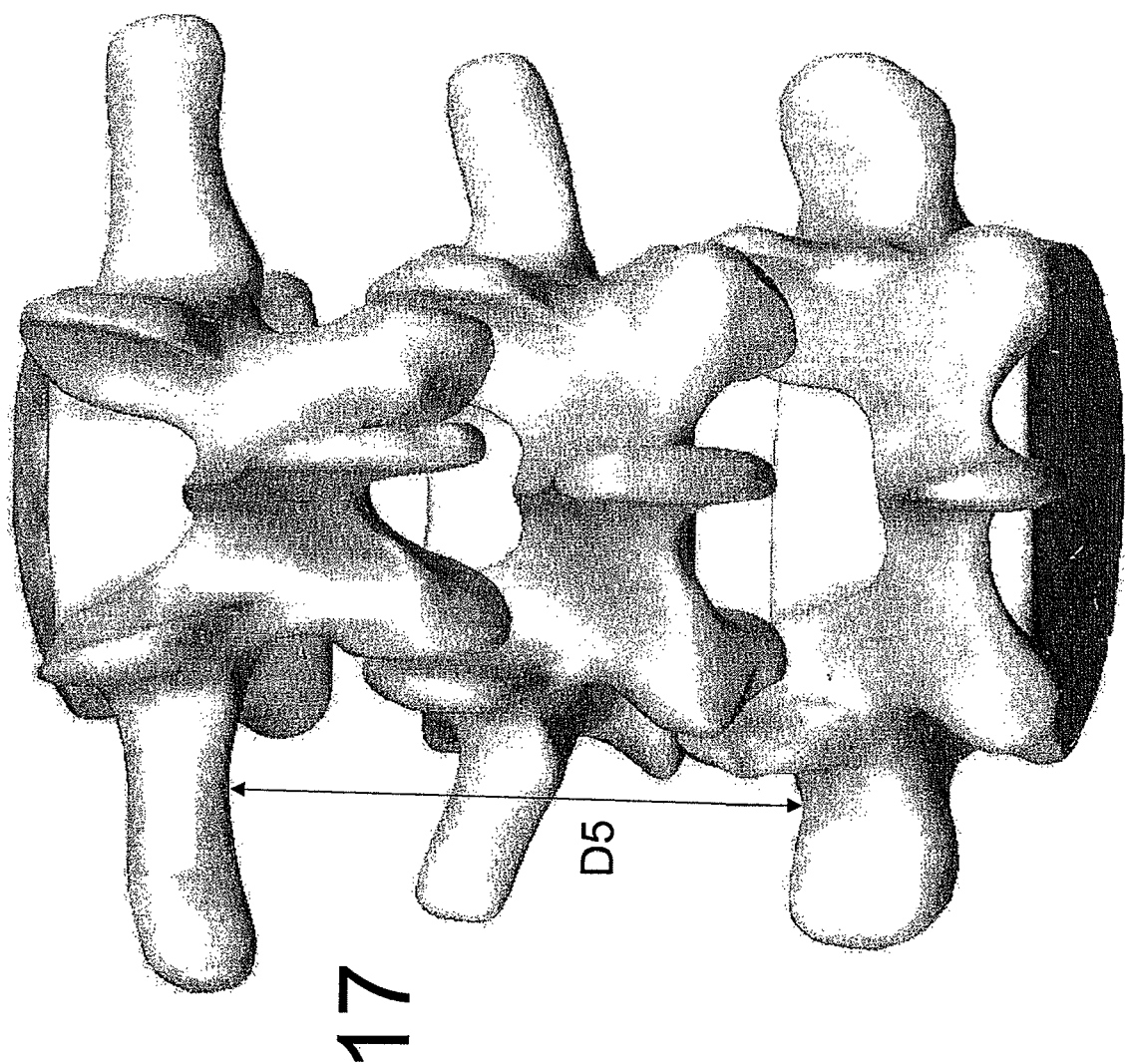
FIG. 17 shows an alternate embodiment.

In another embodiment, extension between a top-most and a bottom-most vertebra within a spinal segment of three or more vertebrae is limited by limiting the distance D5 (FIG. 17) between the transverse process of the upper-most vertebra and the transverse process of the lower-most vertebra. While not shown, the method can be accomplished by anchoring a bone screw 109 or similar fastener to the pedicle portion (or similar bone attachment point) of the intermediate vertebra. A bar is attached to the bone screw and used to span the distance D5 and abut the lower surface of the upper transverse process and the upper surface of the lower transverse process.

Figure 18:
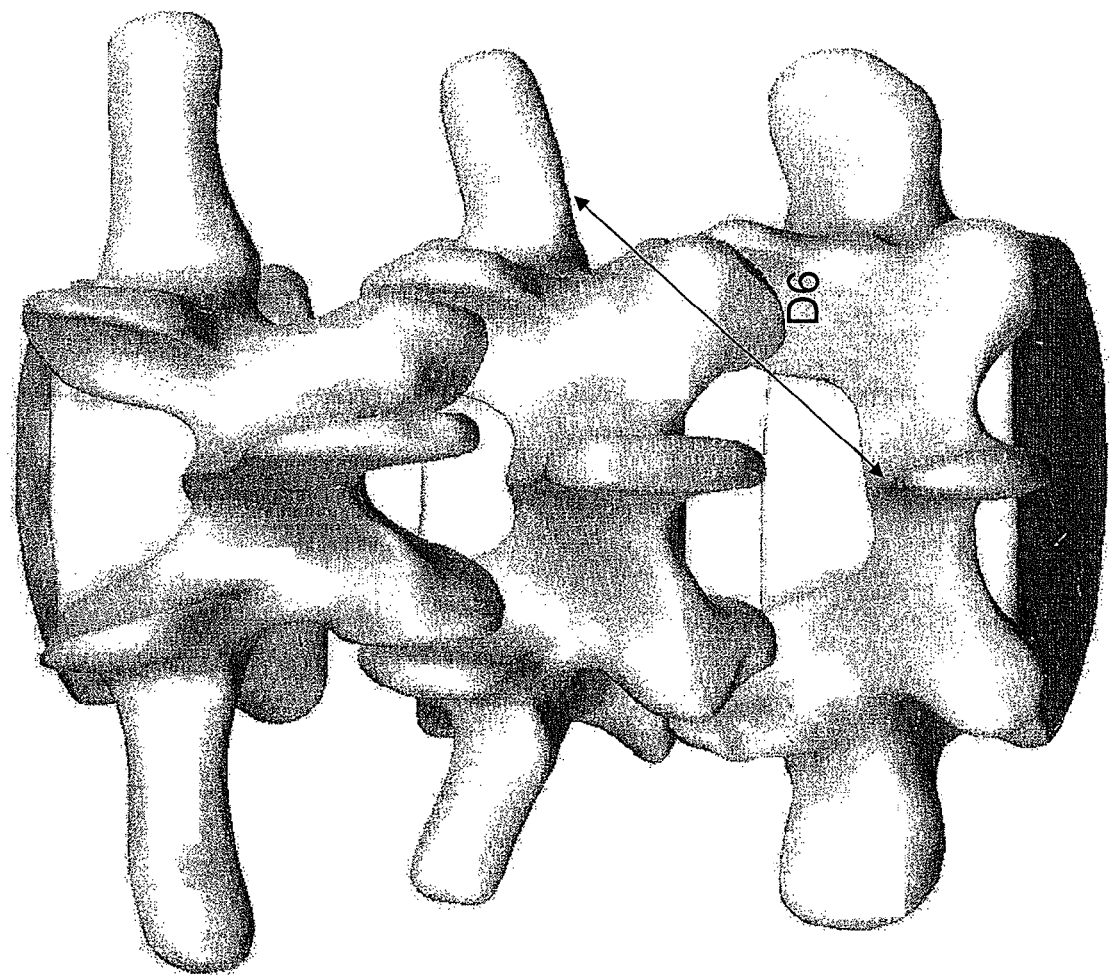
FIG. 18 shows an alternate embodiment.

In another embodiment, extension between a top-most and a bottom-most vertebra within a spinal segment of three or more vertebrae is limited by limiting the distance D6 (FIG. 18) between the transverse process of the upper-most vertebra and the spinous process of the lower-most vertebra. While not shown, this method can be accomplished by anchoring device 612 of FIGS. 8 and 9 with member 514 anchored to the spinous process of the lower-most vertebra and bar 5130 positioned so that abutment bar 5132 abuts the lower aspect of the transverse process of the upper-most vertebra.

Figure 19:
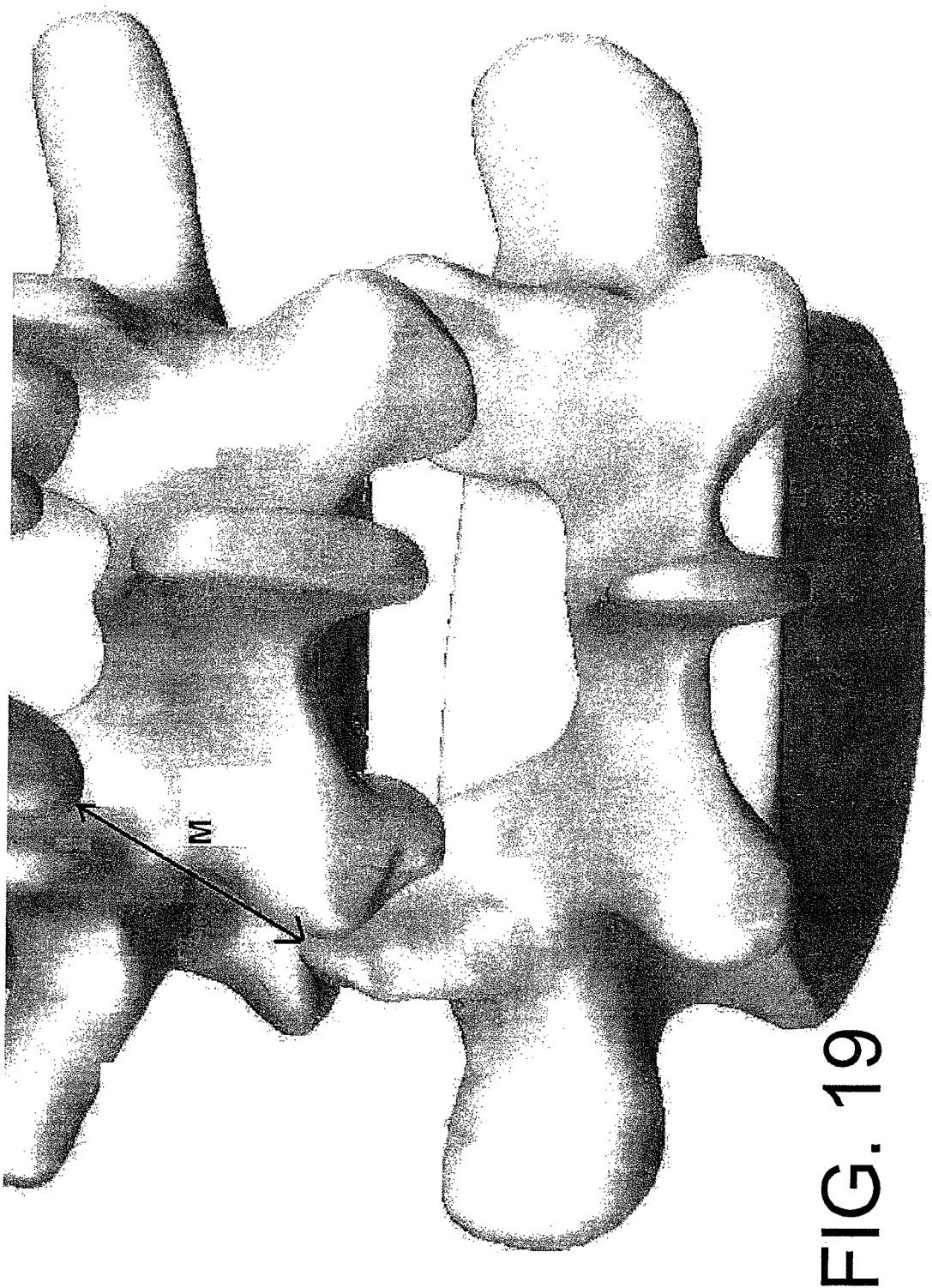
FIG. 19 shows an alternate embodiment.
Figure 20:
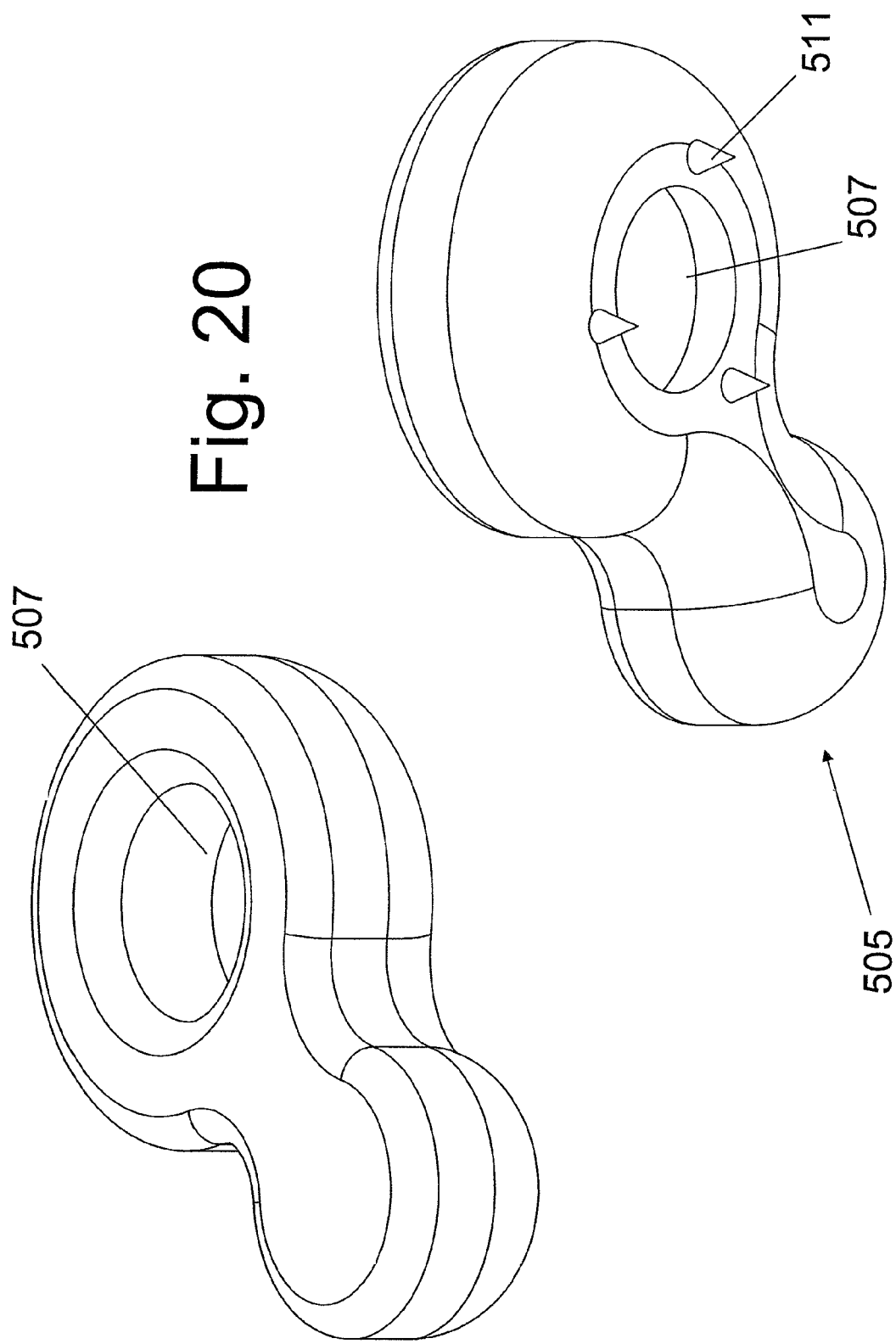
Figure 22:
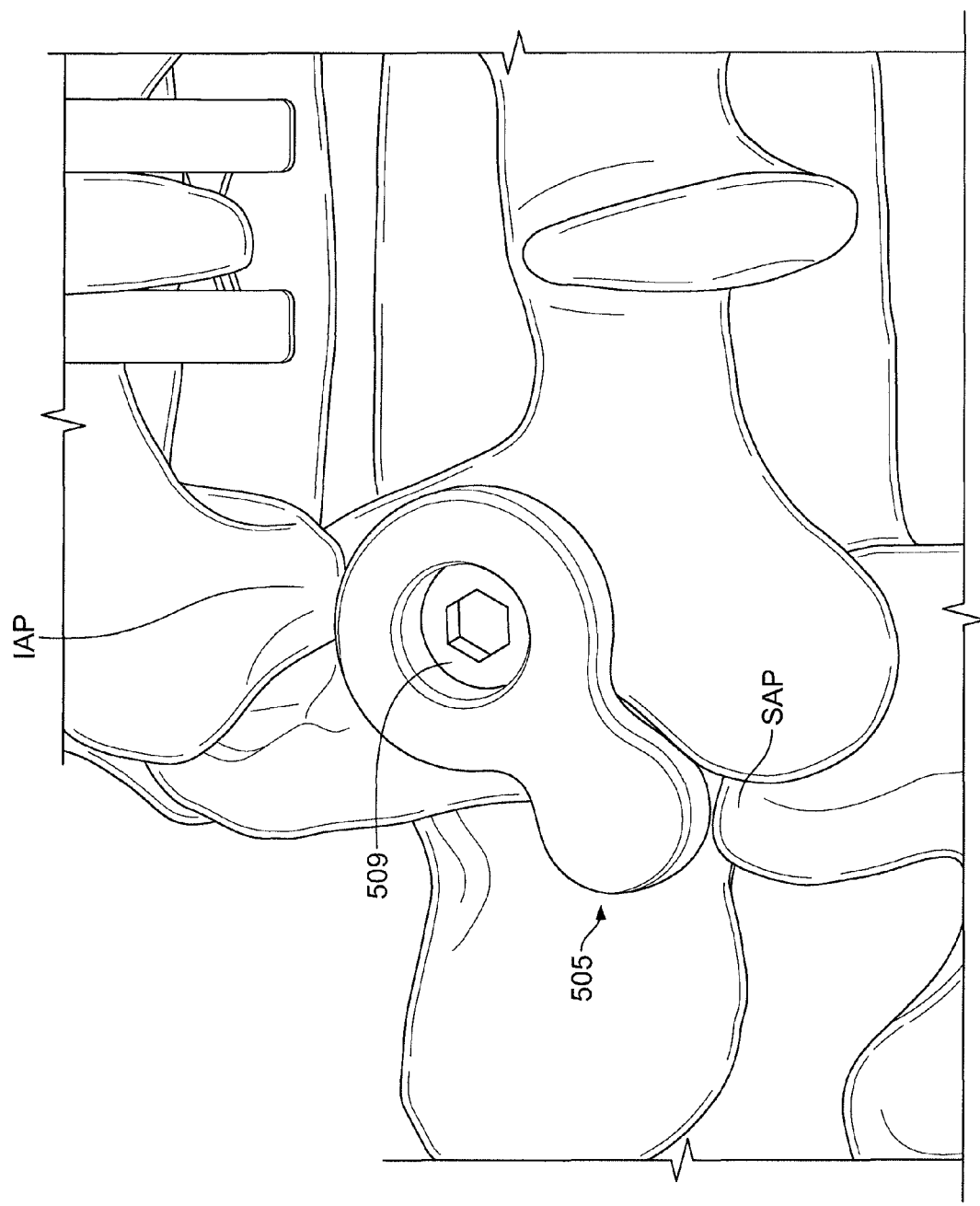
Figure 23:
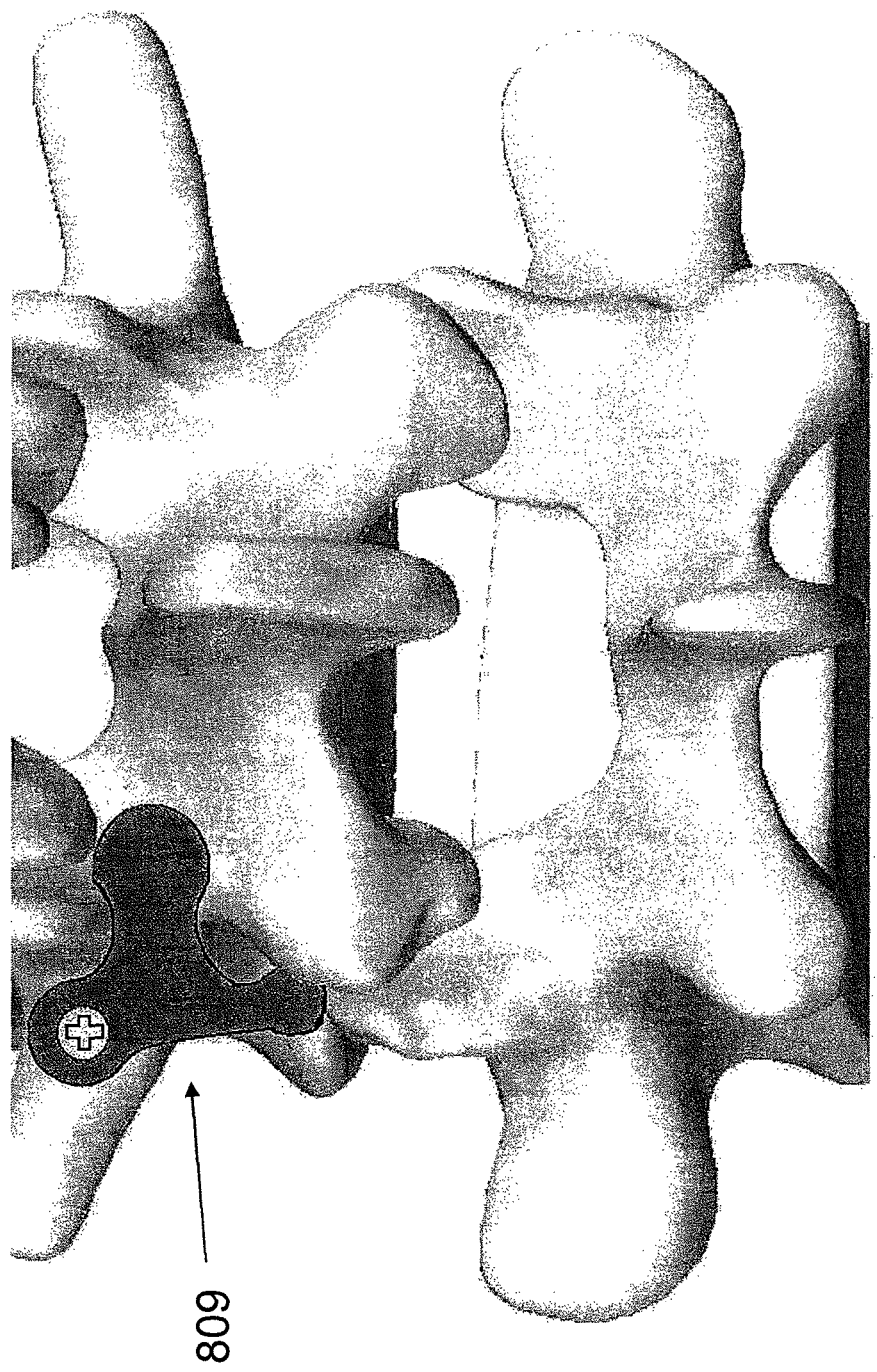
FIG. 23 shows an alternate embodiment.

In another embodiment, extension between a top-most and a bottom-most vertebra within a spinal segment of three or more vertebrae is limited by limiting the distance M (FIG. 19) between the IAP of the upper-most vertebra and the SAP of the lower-most vertebra. As an example, the method can be accomplished by anchoring device 505 of FIGS. 20 and 21 onto the intermediate vertebral bone wherein a protrusion of device 505 abuts the IAP of the upper-most vertebra and another protrusion abuts the SAP of the lower-most vertebra. As shown, device 505 contains a bore hole 507 adapted to accept a bone screw or other fastener. Spikes 511 are adapted to penetrate the underlying bone surface and prevent device rotation. FIG. 22 shows device 505 in use, wherein fastener 509 is anchored to the intermediate vertebral bone (for example, to the pedicle segment of bone) at a point that is medial to the SAP of the intermediate vertebra. FIG. 23 illustrates an alternative but similar device 809, wherein the device is attached to the intermediate vertebra at a point that is lateral to the SAP of the intermediate vertebra.

Figure 24:
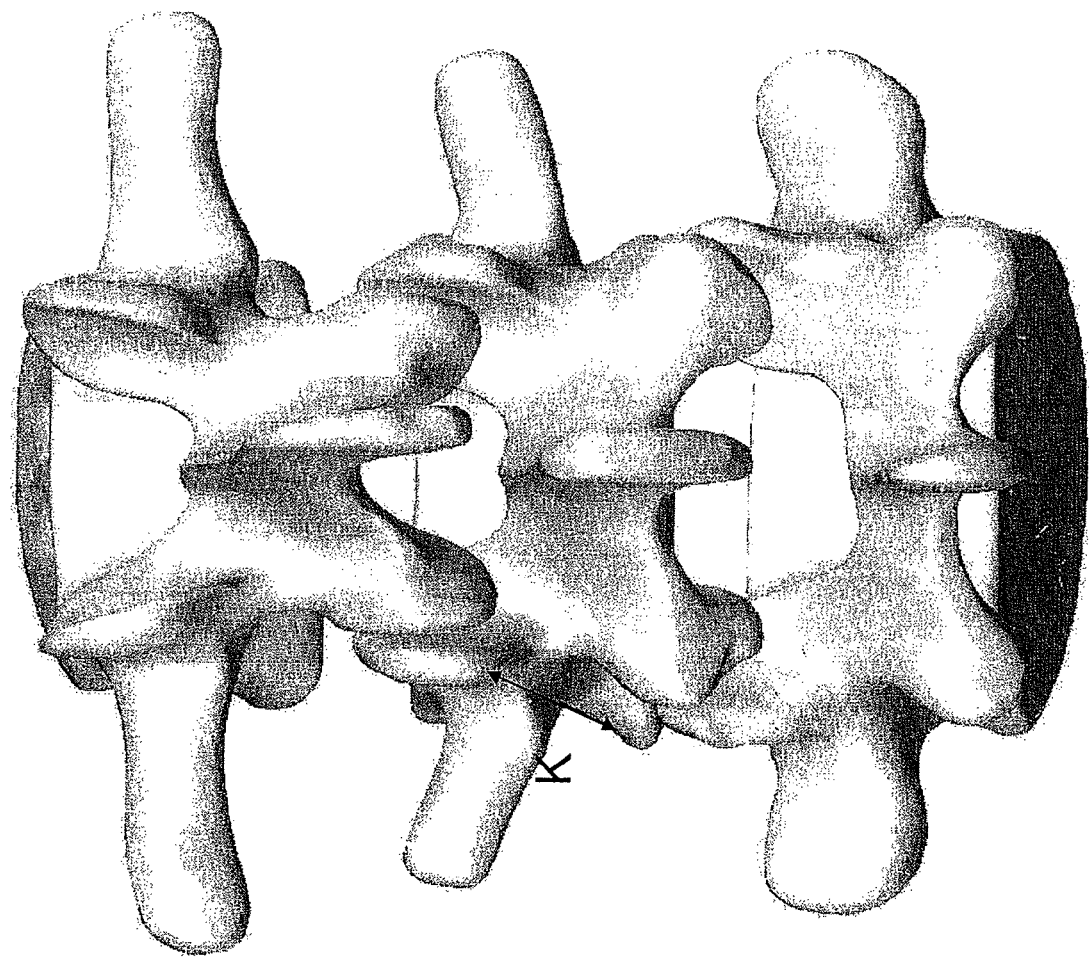
FIG. 24 shows an alternate embodiment.
Figure 25:
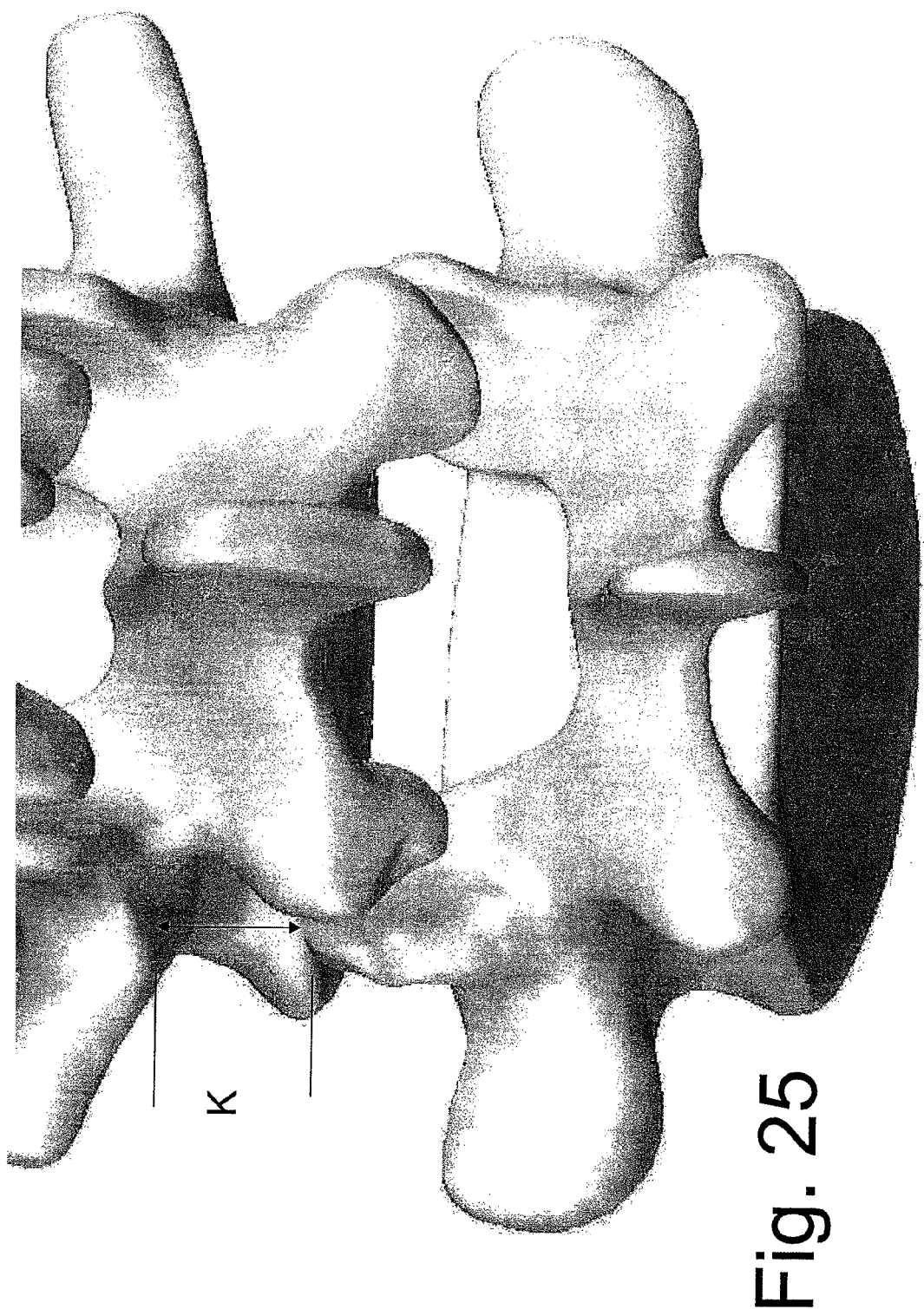
FIG. 25 shows an alternate embodiment.
Figure 26:
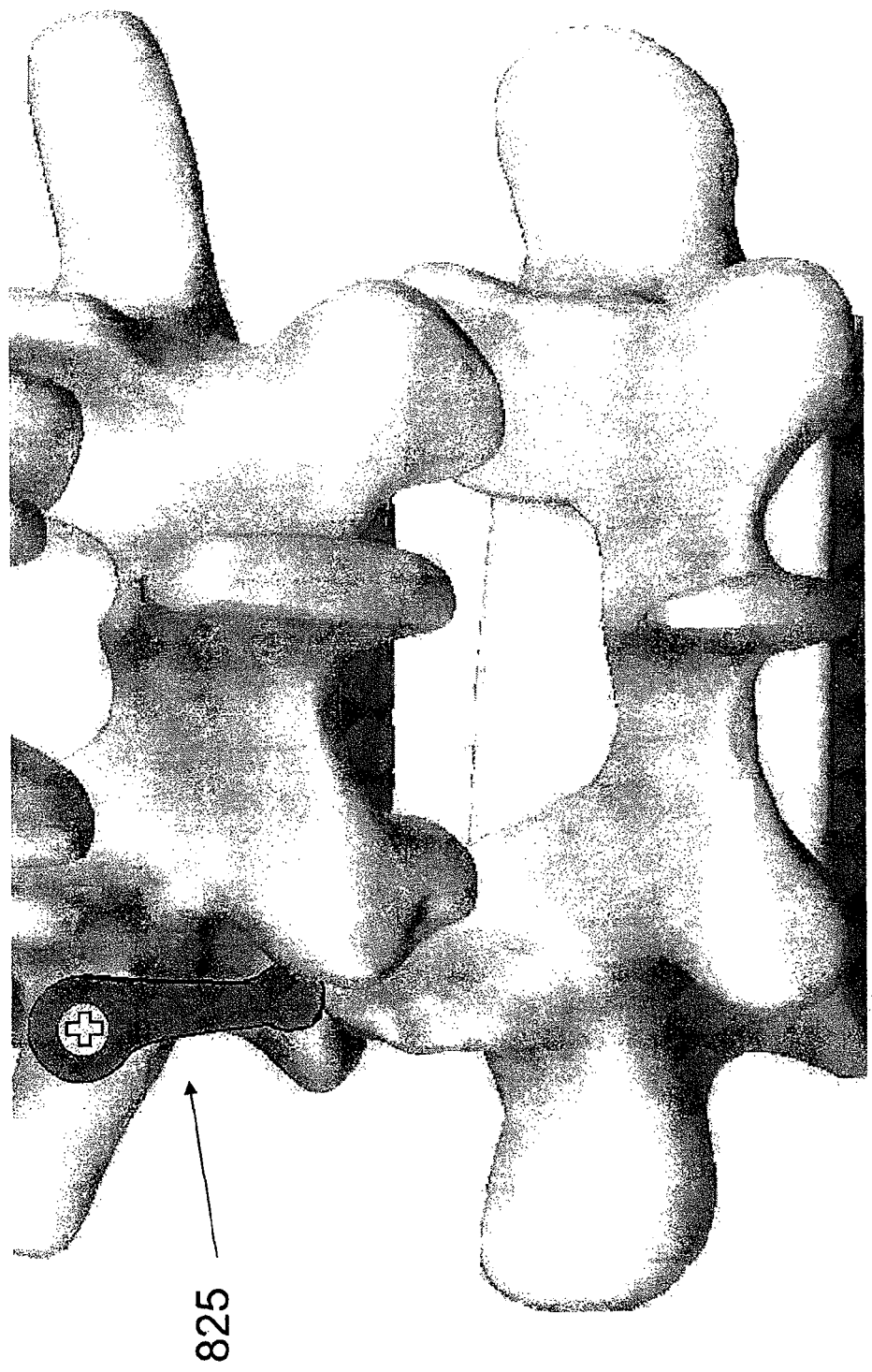
FIG. 26 shows an alternate embodiment.

(Note that extension may be limited between two adjacent vertebrae by limiting the distance K between the superior aspect of the SAP of the lower vertebra and the inferior aspect of the IAP of the upper vertebra—as shown in FIG. 24. Alternatively, distance K may extend from the SAP of the lower vertebra to the transverse process or pedicel portion of the upper vertebra (FIG. 25). As shown in FIG. 26, Device 825 may be implanted to utilize this method. The device may be anchored to the underlying bone using a bone fastener, wherein the fastener enters the pedicle portion of the superior vertebra.)

Figure 27:
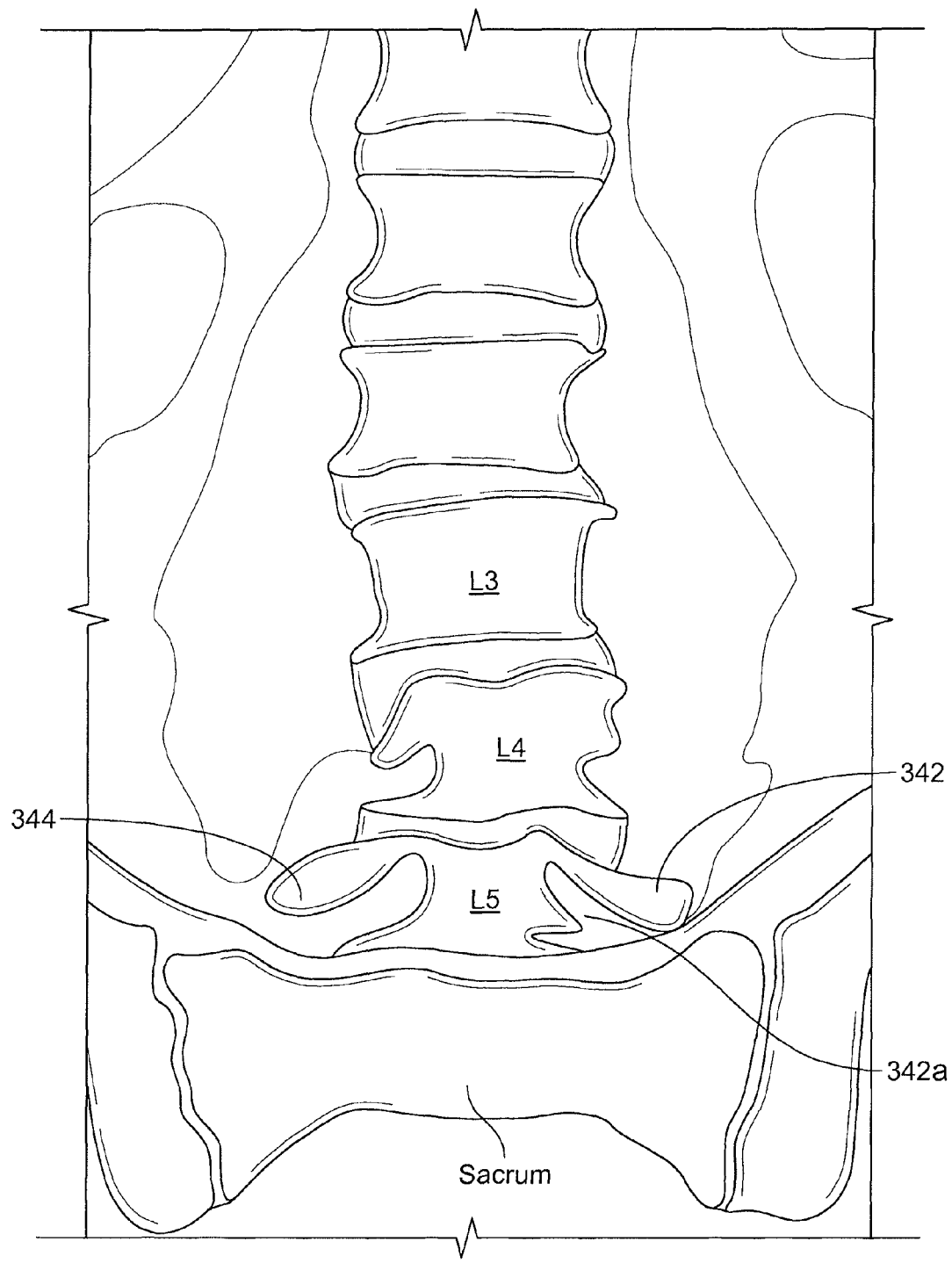
FIG. 27 shows an alternate embodiment.

FIG. 27 illustrates an X-ray examination of a spine with spinal stenosis. Note that the transverse process 342 of the L5 vertebra bone is closer to the sacrum than the contra-lateral transverse process 344. Because of this, the L5 nerve root 342A on the side of transverse process 342 may be trapped and impinged within the stenosed neural foramen. FIGS. 28A illustrate a device and method for decompressing the L5 foraminal stenosis. Implant 42 is inserted between the transverse process of the L5 vertebral bone and the top of the sacral ala (distance 4 of FIG. 3) in order to distract these structures and limit vertebral extension. The implant may be anchored onto the sacral ala or attached to the transverse process (and/or pedicle) of the L5 vertebral bone, but not to both sacrum and L5 bone. In FIG. 28A, the device is anchored to the sacral ala and forms an abutment surface 426 with the transverse process of the L5 vertebra. In this way, extension may be limited but forward flexion of the vertebrae is still permitted.

An exemplary embodiment of implant 42 is shown in FIG. 28B. Device 42 contains a central cavity 422 that is adapted to house a bone graft or bone graft substitute. The device walls may contain a plurality of bore holes 424 that permit communication between the graft material and the bone surface that is adjacent to the device surface. While the device is anchored to a first bone (the sacral ala in FIG. 28A), at least one device wall 426 forms an abutment surface with the second bone (the transverse process of the L5 vertebra in FIG. 28A). In an embodiment, abutment surface 426 contains no holes 424. The device may further contain surface features (ridges, spikes, knurls, bone fastener hole and a bone fastener, and the like) that increase attachment onto the bone to which the device is affixed (sacral ala in the case).

Device 42 is adapted to fuse onto a first (the sacrum or the transverse process of L5, but not both) and form an abutment surface with the second bone. In the illustration, the device is fused to the sacrum and surface 426 of the device abuts the L5 transverse process. Alternatively, a device that affixes onto the L5 vertebral bone (especially into the pedicle portion of L5 using a bone screw or similar fastener) and abuts, but does not attach to, the sacrum may be alternatively used.

Each of the embodiments described above modifies the motion between adjacent vertebras. They preferably limited distraction but preserve at least some flexion within at least one functional spinal unit (FSU) of the implanted spinal segment. It is further contemplated that at least one pair of adjacent vertebra (that is, one FSU) within the implanted spinal segment may be fused together.

While describe as separate embodiments, the various mechanisms may be used in combinations to produce additional assemblies that have not been specifically described herein, but, nevertheless, would fall within the scope of this invention.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with nanotube materials to further impart unique mechanical or biological properties. In addition, any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method to limit the extent of vertebral extension between an upper-most vertebral bone and a lower-most bone of a spinal segment having three or more bony levels which may include the sacrum, comprising:
affixing an orthopedic implant to an intermediate vertebral bone;
abutting a first abutment surface of the orthopedic implant against a superior end surface of an ipsilateral superior articulating process of the lower most bone of the spinal segment;
abutting a second abutment surface of the orthopedic implant against an inferior end surface of an ipsilateral inferior articulating process of the upper-most vertebral bone of the spinal segment; and
limiting the extent of spinal segment extension wherein the abutment surfaces restrict the travel of the superior articulating process of the lower-most bone towards the inferior articulating process of the upper-most bone during vertebral extension, and wherein flexion of the spinal segment is at least partially preserved.

2. A method as in claim 1, wherein the first abutment is separated from being positioned within a facet joint.

3. A method as in claim 1, wherein the totality of the ipsilateral superior articulating process of the lower most bone of the spinal segment is positioned inferior to the first abutment member.

4. A method as in claim 1, wherein the second abutment is separated from being directly positioned within a facet joint.

5. A method as in claim 1, wherein the totality of the ipsilateral inferior articulating process of the upper-most vertebral bone of the spinal segment is positioned superior to the second abutment member.

6. A method as in claim 1, wherein the orthopedic implant is at least partially positioned posterior to the pars interarticularis of the intermediate vertebral bone.

7. A method as in claim 1, wherein orthopedic implant is at least partially positioned inferior to the superior articulating process and superior to the inferior articulating process of the intermediate vertebral bone.

8. A method as in claim 1, wherein the orthopedic implant is at least partially manufactured from a metallic alloy.

9. A method as in claim 1, wherein the orthopedic implant is at least partially manufactured from a plastic material.

10. A method to limit the extent of spinal segment extension between an upper-most vertebral bone and a lower-most bone within a spinal segment of three or more bony levels which may include the sacrum, comprising:
affixing an orthopedic implant to the spinous process of the upper-most vertebral bone;
abutting a first abutment surface of the orthopedic implant against a superior end surface of an ipsilateral superior articulating process of the lower-most bone of the spinal segment, wherein the implant is separated from direct screw fixation into the lower-most bone; and
limiting the extent of spinal segment extension wherein the first abutment surface restricts the travel of the superior articulating process of the lower-most bone towards the spinous process of the upper-most vertebral bone during extension.

11. A method as in claim 10, wherein the first abutment is separated from being positioned within a facet joint.

12. A method as in claim 10, wherein the totality of the ipsilateral superior articulating process of the lower-most bone of the spinal segment is positioned inferior to the first abutment member.

13. A method as in claim 10, wherein the orthopedic implant is comprised of:
A first body extending from a first end to a second end in the direction of a first axis, the first body having a side wall that contains a first bone abutment surface;
a second body extending from a first end to a second end in the direction of a second axis, the second body having a side wall that contains a second bone abutment surface, wherein the second bone abutment surface is substantially aligned to face the first bone abutment surface and wherein a distance between said bone abutment surfaces is variable;
an interconnecting member that movably couples the first and the second bodies, wherein a locking mechanism is disposed between the interconnecting member and at least one of the first or second bodies, and wherein the at least one locking mechanism, when transitioned to a locked state, limits movement between the interconnecting member and said bodies.

14. A method as in claim 10, wherein flexion of the spinal segment is at least partially preserved.

15. A method as in claim 10, wherein the implant is adapted to form a bony fusion with the upper-most vertebral bone.

16. A method as in claim 15, wherein the implant is adapted to fuse onto the spinous process segment of bone.

17. A method as in claim 15, wherein the implant is adapted to fuse onto the lamina segment of bone.

18. A method as in claim 10, wherein the orthopedic implant is at least partially manufactured from a metallic alloy.

19. A method as in claim 10, wherein the orthopedic implant is at least partially manufactured from a plastic material.

20. A method to limit the extent of vertebral extension within a three bone segment containing a sacrum and the two vertebral bones immediately superior to it, comprising:
affixing an orthopedic implant to an intermediate vertebral bone that is positioned immediately superior to the sacrum and immediately inferior to an upper-most vertebral bone of said three bone segment;
positioning a first abutment member of the implant against a superior end surface of an ipsilateral Ala segment of the sacrum;
abutting a second abutment member of the implant against a lower end surface of an ipsilateral inferior articulating process of the upper-most vertebral bone of said three bone segment;
limiting the extent of vertebral extension, wherein the abutment surfaces restrict the travel of the inferior articulating process of upper-most vertebral bone towards the superior end surface of the Ala segment of the sacrum during vertebral extension.

21. A method as in claim 20, wherein the second abutment is separated from being positioned within a facet joint.

22. A method as in claim 20, wherein the totality of the ipsilateral inferior articulating process of the upper-most vertebral bone of the segment is positioned superior to the second abutment member.

23. A method as in claim 20, wherein at least a portion of the orthopedic implant is positioned posterior to the pars interarticularis of the intermediate vertebral bone.

24. A method as in claim 20, wherein at least a portion of the orthopedic implant is positioned inferior to the superior articulating process and superior to the inferior articulating process of the intermediate vertebral bone.

25. A method as in claim 20, wherein the implant is coupled to bone anchor.

26. A method as in claim 25, wherein said bone anchor is affixed to the ipsilateral pedicle of the intermediate vertebral bone.

27. A method as in claim 20, wherein the orthopedic implant is at least partially manufactured from a metallic alloy.

28. A method as in claim 27, wherein the metallic alloy is at least partially comprised of Titanium.

29. A method as in claim 20, wherein the orthopedic implant is at least partially manufactured from a plastic material.

30. A method to limit the extent of vertebral extension between an upper-most vertebral bone and a lower-most bone of a spinal segment having three or more bony levels and which may include the sacrum, comprising:
providing an orthopedic implant, comprising:
a first body extending from a first end to a second end in the direction of a first axis, the first body having a side wall that contains a first bone abutment surface;
a second body extending from a first end to a second end in the direction of a second axis, the second body having a side wall that contains a second bone abutment surface, wherein the second bone abutment surface is substantially aligned to face the first bone abutment surface and wherein a distance between said bone abutment surfaces is variable;
an interconnecting member that movably couples the first and the second bodies, wherein a locking feature is disposed at the region of coupling between the interconnecting member and the first body, and wherein the locking feature is adapted to limit movement between the interconnecting member and the first body when in a locked state;
positioning the implant in proximity to a spinous process of the upper-most vertebral bone;
advancing the first bone abutment surface towards the second bone abutment surface and capturing the spinous process of the upper-most vertebral bone therebetween;
positioning the interconnecting member with a first segment abutting a superior end surface of a right superior articulating process of the lower-most vertebral bone and a second segment abutting a superior end surface of a left superior articulating process of the lower-most vertebral bone;
actuating the locking mechanism of the implant, wherein the locked implant is affixed to the spinous process of the upper-most vertebral bone and separated from direct screw fixation into the lower-most bone.

31. A method as in claim 30, wherein the interconnecting member is separated from being positioned within a facet joint.

32. A method as in claim 30, wherein a portion of the first segment of the interconnecting member is positioned posterior to the right pars interarticularis of the intermediate vertebral bone.

33. A method as in claim 30, wherein a portion of the second segment of the interconnecting member is positioned posterior to the left pars interarticularis of the intermediate vertebral bone.

34. A method as in claim 30, wherein a portion of first segment of the interconnecting member is positioned inferior to the right superior articulating process and superior to the right inferior articulating process of the intermediate vertebral bone.

35. A method as in claim 30, wherein a portion of second segment of the interconnecting member is positioned inferior to the left superior articulating process and superior to the left inferior articulating process of the intermediate vertebral bone.

36. A method as in claim 30, wherein at least one of said first or second bodies contains an internal cavity that is adapted to house a bone forming material.

37. A method as in claim 30, wherein the orthopedic implant is at least partially manufactured from a metallic alloy.

38. A method as in claim 30, wherein the orthopedic implant is at least partially manufactured from a plastic material.

39. A method as in claim 36, wherein the bone forming material that is at least partially contained within the internal cavity is adapted to form a bony fusion with the spinous process of the upper-most vertebral bone.

40. A method as in claim 36, wherein the bone forming material that is at least partially contained within the internal cavity is adapted to form a bony fusion with a lamina segment of the upper-most vertebral bone.

* * * * *